(12) United States Patent
McCullough

(10) Patent No.: US 12,415,039 B2
(45) Date of Patent: Sep. 16, 2025

(54) DRUG DELIVERY DEVICE WITH PROXIMITY SENSOR

(71) Applicant: AMGEN INC., Thousand Oaks, CA (US)

(72) Inventor: Adam B. McCullough, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/410,003

(22) Filed: Jan. 11, 2024

(65) Prior Publication Data

US 2024/0245865 A1 Jul. 25, 2024

Related U.S. Application Data

(63) Continuation of application No. 16/942,733, filed on Jul. 29, 2020, now Pat. No. 11,944,794, which is a
(Continued)

(51) Int. Cl.
*A61M 5/315* (2006.01)
*A61M 5/00* (2006.01)
(Continued)

(52) U.S. Cl.
CPC .......... *A61M 5/31501* (2013.01); *A61M 5/00* (2013.01); *A61M 5/14244* (2013.01);
(Continued)

(58) Field of Classification Search
CPC ................ A61M 5/31501; A61M 5/00; A61M 5/14244; A61M 5/14248; A61M 5/1454;
(Continued)

(56) References Cited

U.S. PATENT DOCUMENTS 4,386,606 A 6/1983 Tretinyak et al.
4,417,889 A 11/1983 Choi
(Continued)

FOREIGN PATENT DOCUMENTS

EP 2716317 A1 4/2014
JP 2009514572 A 4/2009
(Continued)

OTHER PUBLICATIONS

Cohen et al., Combination therapy enhances the inhibition of tumor growth with the fully human anti-type 1 insulin-like growth factor receptor monoclonal antibody CP-751,871, Clin. Cancer Res., 11(5):2063-73 (2005).
(Continued)

*Primary Examiner* — James D Ponton
(74) *Attorney, Agent, or Firm* — MARSHALL, GERSTEIN & BORUN LLP

(57) ABSTRACT

A drug delivery device, in the form of an injector, may include one of a number of systems for limiting the delivery of a medical fluid or drug product in case of movement of (e.g., removal of) the injector relative to the patient as determined by a proximity sensor. The drug delivery system may in the alternative or in addition include systems for indicating the amount of medical fluid or drug product delivered (or not delivered) in case of movement of (e.g., removal of) the injector relative to the patient as determined by the proximity sensor. The injector may be, for example, an on-body injector or an hand-held autoinjector.

18 Claims, 8 Drawing Sheets

Related U.S. Application Data continuation of application No. 15/047,853, filed on Feb. 19, 2016, now Pat. No. 10,765,801, which is a continuation of application No. PCT/US2015/066597, filed on Dec. 18, 2015.

(60) Provisional application No. 62/094,395, filed on Dec. 19, 2014.

(51) Int. Cl.
  *A61M 5/142* (2006.01)
  *A61M 5/145* (2006.01)
  *A61M 5/158* (2006.01)
  *A61M 5/168* (2006.01)
  *A61M 5/20* (2006.01)
  *A61M 5/50* (2006.01)

(52) U.S. Cl.
  CPC ...... *A61M 5/14248* (2013.01); *A61M 5/1454* (2013.01); *A61M 5/20* (2013.01); *A61M 5/2033* (2013.01); *A61M 5/5086* (2013.01); *A61M 2005/14252* (2013.01); *A61M 5/14526* (2013.01); *A61M 2005/1581* (2013.01); *A61M 5/1684* (2013.01); *A61M 5/16881* (2013.01); *A61M 2005/2013* (2013.01); *A61M 2005/2073* (2013.01); *A61M 2205/13* (2013.01); *A61M 2205/33* (2013.01); *A61M 2205/3351* (2013.01); *A61M 2205/50* (2013.01); *A61M 2205/583* (2013.01); *A61M 2205/8225* (2013.01)

(58) Field of Classification Search
  CPC .... A61M 5/20; A61M 5/2033; A61M 5/5086; A61M 5/14526; A61M 5/1684; A61M 5/16881; A61M 2005/14252; A61M 2005/1581; A61M 2005/2013; A61M 2005/2073; A61M 2205/13; A61M 2205/33; A61M 2205/3351; A61M 2205/50; A61M 2205/583; A61M 2205/8225; A61M 5/2046; A61M 5/2053
  See application file for complete search history.

(56) References Cited

U.S. PATENT DOCUMENTS

| | | |
|---|---|---|
| 4,559,038 A | 12/1985 | Berg et al. |
| 4,703,008 A | 10/1987 | Lin |
| 5,441,868 A | 8/1995 | Lin |
| 5,505,706 A | 4/1996 | Maus et al. |
| 5,547,933 A | 8/1996 | Lin |
| 5,582,593 A | 12/1996 | Hultman |
| 5,618,698 A | 4/1997 | Lin |
| 5,621,080 A | 4/1997 | Lin |
| 5,686,292 A | 11/1997 | Schwall et al. |
| 5,756,349 A | 5/1998 | Lin |
| 5,767,078 A | 6/1998 | Johnson et al. |
| 5,773,569 A | 6/1998 | Wrighton et al. |
| 5,789,554 A | 8/1998 | Leung et al. |
| 5,830,851 A | 11/1998 | Wrighton et al. |
| 5,856,298 A | 1/1999 | Strickland |
| 5,879,143 A | 3/1999 | Cote et al. |
| 5,955,422 A | 9/1999 | Lin |
| 5,986,047 A | 11/1999 | Wrighton et al. |
| 6,030,086 A | 2/2000 | Thomas |
| 6,063,053 A | 5/2000 | Castellano et al. |
| 6,183,441 B1 | 2/2001 | Kriesel et al. |
| 6,310,078 B1 | 10/2001 | Connolly et al. |
| 6,355,019 B1 | 3/2002 | Kriesel et al. |
| 6,391,633 B1 | 5/2002 | Stern et al. |
| 6,468,529 B1 | 10/2002 | Schwall et al. |
| 6,562,596 B1 | 5/2003 | Silbiger et al. |
| 6,583,272 B1 | 6/2003 | Bailon |
| 6,586,398 B1 | 7/2003 | Kinstler et al. |
| 6,648,821 B2 | 11/2003 | Lebel et al. |
| 6,740,059 B2 | 5/2004 | Flaherty |
| 6,750,369 B2 | 6/2004 | Connolly et al. |
| 6,756,480 B2 | 6/2004 | Kostenuik et al. |
| 6,803,453 B1 | 10/2004 | Brunkow et al. |
| 6,835,809 B1 | 12/2004 | Liu et al. |
| 6,878,136 B2 | 4/2005 | Fleury et al. |
| 6,900,292 B2 | 5/2005 | Sun et al. |
| 6,918,894 B2 | 7/2005 | Fleury et al. |
| 6,919,426 B2 | 7/2005 | Boone et al. |
| 6,958,705 B2 | 10/2005 | Lebel et al. |
| 6,974,437 B2 | 12/2005 | Lebel et al. |
| 7,030,226 B2 | 4/2006 | Sun et al. |
| 7,037,498 B2 | 5/2006 | Cohen et al. |
| 7,084,245 B2 | 8/2006 | Holmes et al. |
| 7,153,507 B2 | 12/2006 | van de Winkel et al. |
| 7,217,689 B1 | 5/2007 | Elliott et al. |
| 7,220,245 B2 | 5/2007 | Kriesel |
| 7,220,410 B2 | 5/2007 | Kim et al. |
| 7,223,593 B2 | 5/2007 | Coffin |
| 7,510,544 B2 | 3/2009 | Vilks et al. |
| 7,521,048 B2 | 4/2009 | Gliniak et al. |
| 7,537,924 B2 | 5/2009 | Coffin |
| 7,645,263 B2 | 1/2010 | Angel et al. |
| 7,766,873 B2 | 8/2010 | Moberg et al. |
| 7,831,310 B2 | 11/2010 | Lebel et al. |
| 7,871,399 B2 | 1/2011 | Dacquay et al. |
| 7,875,022 B2 | 1/2011 | Wenger et al. |
| 7,951,122 B2 | 5/2011 | Shekalim |
| 7,955,297 B2 * | 6/2011 | Radmer ............ A61M 5/14248 604/93.01 |
| 7,967,773 B2 | 6/2011 | Amborn et al. |
| 7,976,493 B2 | 7/2011 | Carter et al. |
| 7,976,500 B2 | 7/2011 | Adams et al. |
| 7,976,505 B2 | 7/2011 | Hines et al. |
| 7,981,669 B2 | 7/2011 | Coffin et al. |
| 8,016,789 B2 | 9/2011 | Grant et al. |
| 8,128,597 B2 | 3/2012 | Cross et al. |
| 8,147,451 B2 | 4/2012 | Brockman et al. |
| 8,231,577 B2 | 7/2012 | Carter et al. |
| 8,303,535 B2 | 11/2012 | Both et al. |
| 8,361,030 B2 | 1/2013 | Carter |
| 8,414,523 B2 | 4/2013 | Blomquist et al. |
| 8,439,879 B2 | 5/2013 | Shekalim |
| 8,454,557 B1 | 6/2013 | Qi et al. |
| 8,529,500 B2 | 9/2013 | Bingham et al. |
| 8,647,302 B2 | 2/2014 | Briones et al. |
| 8,717,141 B2 | 5/2014 | Eberhart et al. |
| 8,784,380 B2 | 7/2014 | Wall |
| 8,821,454 B2 | 9/2014 | Kriesel et al. |
| 8,905,974 B2 | 12/2014 | Carter et al. |
| 8,998,842 B2 | 4/2015 | Lauchard et al. |
| 9,008,764 B2 | 4/2015 | Larsen |
| 9,114,208 B2 | 8/2015 | Smith et al. |
| 9,132,231 B2 | 9/2015 | Gross et al. |
| 9,211,378 B2 | 12/2015 | Boit et al. |
| 9,999,727 B2 | 6/2018 | O'Connor et al. |
| 10,765,801 B2 | 9/2020 | McCullough |
| 10,799,630 B2 | 10/2020 | McCullough |
| 2001/0027294 A1 | 10/2001 | Kriesell et al. |
| 2001/0039397 A1 | 11/2001 | Kriesell et al. |
| 2002/0155998 A1 | 10/2002 | Young et al. |
| 2003/0023586 A1 | 1/2003 | Knorr |
| 2003/0077753 A1 | 4/2003 | Tischer |
| 2003/0082749 A1 | 5/2003 | Sun et al. |
| 2003/0138421 A1 | 7/2003 | van de Winkel et al. |
| 2003/0143202 A1 | 7/2003 | Binley et al. |
| 2003/0195156 A1 | 10/2003 | Min et al. |
| 2003/0229023 A1 | 12/2003 | Oliner et al. |
| 2003/0235582 A1 | 12/2003 | Singh et al. |
| 2004/0009902 A1 | 1/2004 | Boime et al. |
| 2004/0018191 A1 | 1/2004 | Wang et al. |
| 2004/0035491 A1 | 2/2004 | Castellano |
| 2004/0071694 A1 | 4/2004 | DeVries et al. |
| 2004/0071702 A1 | 4/2004 | van de Winkel et al. |
| 2004/0086503 A1 | 5/2004 | Cohen et al. |
| 2004/0091961 A1 | 5/2004 | Evans et al. |

(56) References Cited

U.S. PATENT DOCUMENTS

| | | |
|---|---|---|
| 2004/0097712 A1 | 5/2004 | Varnum et al. |
| 2004/0143857 A1 | 7/2004 | Young et al. |
| 2004/0157293 A1 | 8/2004 | Evans et al. |
| 2004/0175379 A1 | 9/2004 | DeVries et al. |
| 2004/0175824 A1 | 9/2004 | Sun et al. |
| 2004/0181033 A1 | 9/2004 | Han et al. |
| 2004/0202655 A1 | 10/2004 | Morton et al. |
| 2004/0228859 A1 | 11/2004 | Graus et al. |
| 2004/0229318 A1 | 11/2004 | Heavner |
| 2004/0248815 A1 | 12/2004 | Connolly et al. |
| 2004/0265307 A1 | 12/2004 | Singh et al. |
| 2004/0266690 A1 | 12/2004 | Pool |
| 2005/0008642 A1 | 1/2005 | Graus et al. |
| 2005/0019914 A1 | 1/2005 | Staerk et al. |
| 2005/0020980 A1 | 1/2005 | Inoue et al. |
| 2005/0026834 A1 | 2/2005 | Cox et al. |
| 2005/0027264 A1 | 2/2005 | Fleury et al. |
| 2005/0065472 A1 | 3/2005 | Cindrich et al. |
| 2005/0074821 A1 | 4/2005 | Wild et al. |
| 2005/0084906 A1 | 4/2005 | Goetsch et al. |
| 2005/0096461 A1 | 5/2005 | Cox |
| 2005/0107297 A1 | 5/2005 | Holmes et al. |
| 2005/0107591 A1 | 5/2005 | Cox |
| 2005/0112694 A1 | 5/2005 | Carter et al. |
| 2005/0118643 A1 | 6/2005 | Burgess et al. |
| 2005/0124045 A1 | 6/2005 | Sun et al. |
| 2005/0124564 A1 | 6/2005 | Binley et al. |
| 2005/0136063 A1 | 6/2005 | Wang et al. |
| 2005/0137329 A1 | 6/2005 | Holmes et al. |
| 2005/0142642 A1 | 6/2005 | Sun et al. |
| 2005/0143292 A1 | 6/2005 | DeFrees et al. |
| 2005/0153879 A1 | 7/2005 | Svetina et al. |
| 2005/0158822 A1 | 7/2005 | Pecker |
| 2005/0158832 A1 | 7/2005 | Young et al. |
| 2005/0170457 A1 | 8/2005 | Pool et al. |
| 2005/0181359 A1 | 8/2005 | Optelten et al. |
| 2005/0181482 A1 | 8/2005 | Meade et al. |
| 2005/0186203 A1 | 8/2005 | Singh et al. |
| 2005/0192211 A1 | 9/2005 | Gillies et al. |
| 2005/0202538 A1 | 9/2005 | Gillies et al. |
| 2005/0227289 A1 | 10/2005 | Reilly et al. |
| 2005/0244408 A1 | 11/2005 | Cohen et al. |
| 2005/0244409 A1 | 11/2005 | Erickson-Miller et al. |
| 2005/0249728 A1 | 11/2005 | Singh et al. |
| 2006/0040358 A1 | 2/2006 | Ligensa et al. |
| 2006/0088906 A1 | 4/2006 | DeFrees et al. |
| 2006/0111279 A1 | 5/2006 | DeFrees et al. |
| 2006/0135431 A1 | 6/2006 | Min et al. |
| 2007/0038181 A1 | 2/2007 | Melamud et al. |
| 2007/0066939 A1 | 3/2007 | Krulevitch et al. |
| 2007/0100288 A1 | 5/2007 | Bozeman et al. |
| 2007/0110747 A1 | 5/2007 | Paszty et al. |
| 2007/0219480 A1 | 9/2007 | Kamen et al. |
| 2007/0250019 A1 | 10/2007 | Fleury et al. |
| 2007/0253951 A1 | 11/2007 | Ng et al. |
| 2008/0091139 A1 | 4/2008 | Srinivasan et al. |
| 2008/0132844 A1 | 6/2008 | Peterson et al. |
| 2008/0166352 A1 | 7/2008 | Siu et al. |
| 2008/0195056 A1 | 8/2008 | Bishop et al. |
| 2008/0221523 A1 | 9/2008 | Moberg et al. |
| 2008/0234625 A1 | 9/2008 | Dacquay et al. |
| 2008/0262427 A1 | 10/2008 | Hommann |
| 2008/0281273 A1 | 11/2008 | Angel et al. |
| 2009/0043290 A1 | 2/2009 | Villegas et al. |
| 2009/0082730 A1 | 3/2009 | Nguyen et al. |
| 2009/0088690 A1 | 4/2009 | Carter et al. |
| 2009/0099525 A1 | 4/2009 | Lawson |
| 2009/0156989 A1 | 6/2009 | Carter et al. |
| 2009/0177142 A1 | 7/2009 | Blomquist et al. |
| 2009/0182277 A1 | 7/2009 | Carter |
| 2009/0192471 A1 | 7/2009 | Carter et al. |
| 2009/0234106 A1 | 9/2009 | Han et al. |
| 2009/0240240 A1 | 9/2009 | Hines et al. |
| 2009/0326472 A1 | 12/2009 | Carter et al. |
| 2010/0010418 A1 | 1/2010 | Nisato |
| 2010/0094222 A1 | 4/2010 | Grant et al. |
| 2010/0121274 A1 | 5/2010 | Oh et al. |
| 2010/0137801 A1 | 6/2010 | Streit et al. |
| 2010/0152658 A1 | 6/2010 | Hanson et al. |
| 2010/0152666 A1 | 6/2010 | Carter et al. |
| 2010/0166768 A1 | 7/2010 | Sleeman et al. |
| 2010/0198182 A1 | 8/2010 | Lanigan et al. |
| 2010/0198183 A1 | 8/2010 | Lanigan et al. |
| 2010/0253476 A1 | 10/2010 | Poutiatine et al. |
| 2010/0286467 A1 | 11/2010 | Pesach et al. |
| 2011/0022002 A1 | 1/2011 | Hanson et al. |
| 2011/0066012 A1 | 3/2011 | Hanson et al. |
| 2011/0077614 A1 | 3/2011 | Shay |
| 2011/0112484 A1 | 5/2011 | Carter et al. |
| 2011/0118672 A1 | 5/2011 | Hanson et al. |
| 2011/0160696 A1 | 6/2011 | Hoss |
| 2011/0166512 A1* | 7/2011 | Both ................ A61M 5/14248 604/152 |
| 2011/0205065 A1 | 8/2011 | Strachan et al. |
| 2011/0218489 A1 | 9/2011 | Mastrototaro et al. |
| 2011/0224601 A1 | 9/2011 | Shekalim |
| 2011/0230838 A1 | 9/2011 | Adams et al. |
| 2011/0313351 A1* | 12/2011 | Kamen ............... A61M 5/1452 604/67 |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029385 A1 | 2/2012 | Chong et al. |
| 2012/0041370 A1 | 2/2012 | Moberg et al. |
| 2012/0041415 A1 | 2/2012 | Estes et al. |
| 2012/0078170 A1 | 3/2012 | Smith et al. |
| 2012/0078181 A1 | 3/2012 | Smith et al. |
| 2012/0078182 A1 | 3/2012 | Smith et al. |
| 2012/0078184 A1 | 3/2012 | Smith et al. |
| 2012/0078185 A1 | 3/2012 | Smith et al. |
| 2012/0078217 A1 | 3/2012 | Smith et al. |
| 2012/0116309 A1 | 5/2012 | Bazargan et al. |
| 2012/0209194 A1 | 8/2012 | Lanigan et al. |
| 2012/0209196 A1 | 8/2012 | Lanigan et al. |
| 2012/0310169 A1 | 12/2012 | Sonderegger et al. |
| 2012/0310173 A1 | 12/2012 | Sonderegger |
| 2012/0310175 A1 | 12/2012 | Vedrine et al. |
| 2012/0323183 A1 | 12/2012 | Peterson et al. |
| 2013/0006195 A1 | 1/2013 | Sonderegger et al. |
| 2013/0046239 A1 | 2/2013 | Gonnelli et al. |
| 2013/0090625 A1 | 4/2013 | Moberg et al. |
| 2013/0226086 A1 | 8/2013 | Davies et al. |
| 2013/0253434 A1 | 9/2013 | Cabiri |
| 2013/0283196 A1 | 10/2013 | Farnan et al. |
| 2013/0289484 A1 | 10/2013 | Bazargan et al. |
| 2013/0332874 A1 | 12/2013 | Rosinko et al. |
| 2013/0338589 A1 | 12/2013 | Cindrich et al. |
| 2014/0025002 A1 | 1/2014 | Qi et al. |
| 2014/0035604 A1 | 2/2014 | Paul et al. |
| 2014/0046259 A1 | 2/2014 | Reber et al. |
| 2014/0052096 A1 | 2/2014 | Searle et al. |
| 2014/0074062 A1 | 3/2014 | Caffey et al. |
| 2014/0088549 A1 | 3/2014 | Cole et al. |
| 2014/0100544 A1 | 4/2014 | Hwang |
| 2014/0114251 A1 | 4/2014 | Miyazaki |
| 2014/0114252 A1 | 4/2014 | Patel et al. |
| 2014/0121598 A1 | 5/2014 | Katase |
| 2014/0128815 A1 | 5/2014 | Cabiri et al. |
| 2014/0135694 A1 | 5/2014 | Moberg et al. |
| 2014/0135695 A1 | 5/2014 | Grant et al. |
| 2014/0142499 A1 | 5/2014 | Moberg et al. |
| 2014/0148784 A1 | 5/2014 | Anderson et al. |
| 2014/0180210 A1 | 6/2014 | Niklaus et al. |
| 2014/0200510 A1 | 7/2014 | Agard et al. |
| 2014/0207104 A1 | 7/2014 | Vouillamoz et al. |
| 2014/0207106 A1 | 7/2014 | Bechmann et al. |
| 2014/0207122 A1 | 7/2014 | Villegas et al. |
| 2014/0213975 A1 | 7/2014 | Clemente et al. |
| 2014/0221914 A1 | 8/2014 | Calasso |
| 2014/0221974 A1 | 8/2014 | Bechmann et al. |
| 2014/0243749 A1 | 8/2014 | Edwards et al. |
| 2014/0249500 A1 | 9/2014 | Estes |
| 2014/0276423 A1 | 9/2014 | Lecanu-Fayet |
| 2014/0296782 A1 | 10/2014 | Ulrich et al. |

(56) References Cited

U.S. PATENT DOCUMENTS

| | | |
|---|---|---|
| 2014/0296787 A1 | 10/2014 | Agard et al. |
| 2014/0330243 A1 | 11/2014 | Kietzmann et al. |
| 2014/0364808 A1 | 12/2014 | Niklaus et al. |
| 2014/0371675 A1 | 12/2014 | Hegland et al. |
| 2015/0005703 A1 | 1/2015 | Hutchinson et al. |
| 2015/0011939 A1 | 1/2015 | Marbet et al. |
| 2015/0011965 A1 | 1/2015 | Cabiri |
| 2015/0011973 A1 | 1/2015 | Edwards et al. |
| 2015/0011976 A1 | 1/2015 | Vouillamoz et al. |
| 2015/0018768 A1 | 1/2015 | Gray et al. |
| 2015/0025457 A1 | 1/2015 | Moberg et al. |
| 2015/0057615 A1 | 2/2015 | Mernoe, V et al. |
| 2015/0065958 A1 | 3/2015 | Teutsch et al. |
| 2015/0065959 A1 | 3/2015 | Carter et al. |
| 2015/0080799 A1 | 3/2015 | Schneider et al. |
| 2015/0080843 A1 | 3/2015 | Yodfat et al. |
| 2015/0094684 A1 | 4/2015 | Kriesel et al. |
| 2015/0133855 A1 | 5/2015 | Smith et al. |
| 2015/0151082 A1 | 6/2015 | Gescheit |
| 2015/0165113 A1 | 6/2015 | Lanigan et al. |
| 2015/0174324 A1 | 6/2015 | Wurmbauer et al. |
| 2015/0182688 A1 | 7/2015 | Dhami |
| 2015/0182689 A1 | 7/2015 | Dhami |
| 2015/0190574 A1 | 7/2015 | Gravesen et al. |
| 2015/0231328 A1 | 8/2015 | Mandro et al. |
| 2015/0265764 A1 | 9/2015 | Weber et al. |
| 2015/0273151 A1 | 10/2015 | McLoughlin et al. |
| 2015/0306307 A1 | 10/2015 | Cole et al. |

FOREIGN PATENT DOCUMENTS

| | | |
|---|---|---|
| JP | 2012-501771 A | 1/2012 |
| JP | 2013-519471 A | 5/2013 |
| JP | 2013-539684 A | 10/2013 |
| JP | 2014525326 A | 9/2014 |
| WO | WO-91/05867 A1 | 5/1991 |
| WO | WO-95/05465 A1 | 2/1995 |
| WO | WO-96/38557 A1 | 12/1996 |
| WO | WO-97/21457 A1 | 6/1997 |
| WO | WO-9723252 A1 | 7/1997 |
| WO | WO-99/66054 A2 | 12/1999 |
| WO | WO-00/24893 A2 | 5/2000 |
| WO | WO-00/61637 A1 | 10/2000 |
| WO | WO-01/31007 A2 | 5/2001 |
| WO | WO-01/36489 A2 | 5/2001 |
| WO | WO-01/81405 A2 | 11/2001 |
| WO | WO-02/14356 A2 | 2/2002 |
| WO | WO-02/19963 A2 | 3/2002 |
| WO | WO-02/20034 A1 | 3/2002 |
| WO | WO-02/49673 A2 | 6/2002 |
| WO | WO-02/085940 A2 | 10/2002 |
| WO | WO-03/029291 A2 | 4/2003 |
| WO | WO-03/030833 A2 | 4/2003 |
| WO | WO-03/055526 A2 | 7/2003 |
| WO | WO-03/057134 A2 | 7/2003 |
| WO | WO-03/059951 A2 | 7/2003 |
| WO | WO-03/084477 A2 | 10/2003 |
| WO | WO-03/094858 A2 | 11/2003 |
| WO | WO-2004/002417 A2 | 1/2004 |
| WO | WO-2004/002424 A2 | 1/2004 |
| WO | WO-2004/009627 A1 | 1/2004 |
| WO | WO-2004/018667 A1 | 3/2004 |
| WO | WO-2004/024761 A1 | 3/2004 |
| WO | WO-2004/033651 A2 | 4/2004 |
| WO | WO-2004/035603 A2 | 4/2004 |
| WO | WO-2004/043382 A2 | 5/2004 |
| WO | WO-2004/058988 A2 | 7/2004 |
| WO | WO-2004/101600 A2 | 11/2004 |
| WO | WO-2004/101606 A2 | 11/2004 |
| WO | WO-2004/101611 A2 | 11/2004 |
| WO | WO-2004/106373 A1 | 12/2004 |
| WO | WO-2005/001025 A2 | 1/2005 |
| WO | WO-2005/001136 A1 | 1/2005 |
| WO | WO-2005/016970 A2 | 2/2005 |
| WO | WO-2005/017107 A2 | 2/2005 |
| WO | WO-2005/021579 A2 | 3/2005 |
| WO | WO-2005/025606 A1 | 3/2005 |
| WO | WO-2005/032460 A2 | 4/2005 |
| WO | WO-2005/047331 A2 | 5/2005 |
| WO | WO-2005/051327 A2 | 6/2005 |
| WO | WO-2005/058967 A2 | 6/2005 |
| WO | WO-2005/063808 A1 | 7/2005 |
| WO | WO-2005/063809 A1 | 7/2005 |
| WO | WO-2005/070451 A1 | 8/2005 |
| WO | WO-2005/081687 A2 | 9/2005 |
| WO | WO-2005/084711 A1 | 9/2005 |
| WO | WO-2005/092369 A2 | 10/2005 |
| WO | WO-2005/100403 A2 | 10/2005 |
| WO | WO-2005/103076 A2 | 11/2005 |
| WO | WO-2006/02646 A2 | 1/2006 |
| WO | WO-2006/013472 A2 | 2/2006 |
| WO | WO-2006/029094 A2 | 3/2006 |
| WO | WO-2006/050959 A2 | 5/2006 |
| WO | WO-2006/069202 A2 | 6/2006 |
| WO | WO-2006/081171 A1 | 8/2006 |
| WO | WO-2006/138729 A2 | 12/2006 |
| WO | WO-2007/000328 A1 | 1/2007 |
| WO | WO-2007/011941 A2 | 1/2007 |
| WO | WO-2007/012614 A2 | 2/2007 |
| WO | WO-2008/057457 A2 | 5/2008 |
| WO | WO-2008/057458 A2 | 5/2008 |
| WO | WO-2008/057459 A2 | 5/2008 |
| WO | WO-2008/063382 A2 | 5/2008 |
| WO | WO-2008/125623 A2 | 10/2008 |
| WO | WO-2008/133647 A2 | 11/2008 |
| WO | WO-2009/055783 A2 | 4/2009 |
| WO | WO-2009/100297 A1 | 8/2009 |
| WO | WO-2009/100318 A1 | 8/2009 |
| WO | WO-2010/018411 A1 | 2/2010 |
| WO | WO-2010/029513 A2 | 3/2010 |
| WO | WO-2010/077854 A1 | 7/2010 |
| WO | WO-2011/037791 A1 | 3/2011 |
| WO | WO-2011036294 A1 | 3/2011 |
| WO | WO-2011/053759 A1 | 5/2011 |
| WO | WO-2011/053783 A2 | 5/2011 |
| WO | WO-2011/072263 A1 | 6/2011 |
| WO | WO-2011/101375 A1 | 8/2011 |
| WO | WO-2011/111007 A2 | 9/2011 |
| WO | WO-2012/032411 A2 | 3/2012 |
| WO | WO-2012/045836 A2 | 4/2012 |
| WO | WO-2012/054438 A1 | 4/2012 |
| WO | WO-2012/088313 A1 | 6/2012 |
| WO | WO-2012/101251 A1 | 8/2012 |
| WO | WO-2012/101252 A2 | 8/2012 |
| WO | WO-2012/101253 A1 | 8/2012 |
| WO | WO-2012/109530 A1 | 8/2012 |
| WO | WO-2013/075773 A2 | 5/2013 |
| WO | WO-2014047657 A2 | 3/2014 |
| WO | WO-2014/066256 A1 | 5/2014 |
| WO | WO-2014/095424 A1 | 6/2014 |
| WO | WO-2014/116998 A2 | 7/2014 |

OTHER PUBLICATIONS

European Patent Application No. 15817689.1, Communication Pursuant to Article 94(3) EPC, dated Oct. 26, 2018.

European Patent Application No. 15820801.7, Communication Pursuant to Article 94(3) EPC, May 27, 2020.

European Patent Application No. 20160603.5, Extended European Search Report, May 13, 2020.

International Preliminary Report on Patentability and Written Opinion for International Application No. PCT/US2015/064869, dated Jun. 20, 2017.

International Preliminary Report on Patentability and Written Opinion of International Application No. PCT/US2015/066597, dated Jun. 20, 2017.

International Search Report for PCT/US2015/064869 dated Mar. 17, 2016.

International Search Report for PCT/US2015/066597, dated Jun. 9, 2016.

Japanese Patent Application No. 2017-532778, Notice of Rejection, mailed Aug. 20, 2019.

(56) References Cited

OTHER PUBLICATIONS

Japanese Patent Application No. 2017-532785, Notice of Rejection, mailed Jul. 31, 2018.
Japanese Patent Application No. 2017-532785, Second Official Action, dated Mar. 5, 2019.
Liu et al., Preclinical evaluation of herpes simplex virus armed with granulocyte-macrophage colony-stimulating factor in pancreatic carcinoma, World J. Gastroenterology, 19:5138-43 (2013).
Lu et al., Simultaneous blockade of both the epidermal growth factor receptor and the insulin-like growth factor receptor signaling pathways in cancer cells with a fully human recombinant bispecific antibody, J. Biol. Chem., 279(4):2856-65 (2004).
Maloney et al., An anti-insulin-like growth factor I receptor antibody that is a potent inhibitor of cancer cell proliferation, Cancer Res., 63(16):5073-83 (2003).
Partial International Search Report for application No. PCT/US2015/066597, Mar. 29, 2016.
U.S. Appl. No. 15/040,361, Final Office Action, dated Jun. 26, 2020.
U.S. Appl. No. 15/040,361, Nonfinal Office Action, dated Jan. 6, 2020.
U.S. Appl. No. 15/047,853, Final Office Action, dated Dec. 6, 2018.
U.S. Appl. No. 15/047,853, Final Office Action, dated Jan. 7, 2020.
U.S. Appl. No. 15/047,853, Nonfinal Office Action, dated Jun. 26, 2019.
U.S. Appl. No. 15/047,853, Nonfinal Office Action, dated May 16, 2018.
U.S. Appl. No. 15/522,345, Final Office Action, dated Jan. 21, 2020.
U.S. Appl. No. 15/522,345, Nonfinal Office Action, dated Jul. 19, 2019.
U.S. Appl. No. 15/522,387, Final Office Action, dated Apr. 11, 2019.
U.S. Appl. No. 15/522,387, Final Office Action, dated Mar. 23, 2020.
U.S. Appl. No. 15/522,387, Nonfinal Office Action, dated Dec. 12, 2018.
U.S. Appl. No. 15/522,387, Nonfinal Office Action, dated Oct. 10, 2019.
Varghese et al., Oncolytic herpes simplex virus vectors for cancer virotherapy, Cancer Gene Ther., 9(12):967-78 (2002).
Written Opinion of the International Searching Authority, for International Application PCT/US2015/066597, dated Jun. 23, 2016.
Written Opinion of the International Searching Authority, International Application PCT/US2015/064869, dated Jun. 23, 2016.
Japanese Patent Application No. 2020-032832, Office Action, dated Mar. 2, 2021.
European Patent Application No. 21157878.6, Extended European Search Report, dated Apr. 7, 2021.
Japanese Patent Application No. 2020-032832, Decision of Rejection, mailed Nov. 30, 2021.
Japanese Patent Application No. 2022-047935, Office Action, dated Mar. 7, 2023.
Non-final Office Action, U.S. Appl. No. 16/942,733, mailed Jun. 14, 2023.
European Patent Application No. 20160603.5, Communication Pursuant to Article 93(3) EPC, dated Nov. 21, 2024.

\* cited by examiner

DRUG DELIVERY DEVICE WITH PROXIMITY SENSOR

CROSS-REFERENCE TO RELATED APPLICATIONS

This is a continuation of U.S. Ser. No. 16/942,733, filed Jul. 29, 2020, which is a continuation of U.S. patent application Ser. No. 15/047,853, filed Feb. 19, 2016, which is a continuation of PCT/US2015/066597, filed Dec. 18, 2015, which claims priority to U.S. Provisional Patent Application No. 62/094,395, filed Dec. 19, 2014, the entire contents of each of which are hereby incorporated by reference.

FIELD OF THE DISCLOSURE

This disclosure is directed to a drug delivery device and, in particular, to a drug delivery device that limits drug delivery in accordance with the state of a proximity sensor.

BACKGROUND

Medical fluids and drug products (e.g., drugs) can be administered to a patient through the use of drug delivery devices, such as autoinjectors or on-body injectors or infusers. These devices may replace delivery systems using the combination of a syringe and a vial of the medical fluid or drug product or a pre-filled syringe. Autoinjectors and on-body injectors may be used to automate the needle or cannula insertion and the drug delivery or administration process, thereby simplifying the process for certain patient groups or sub-groups for which use of the syringe/vial combination or pre-filled syringe systems would be disadvantageous, such as groups or sub-groups demonstrating physiological or psychological impediment.

In some instances, after automated insertion of the needle or cannula, the autoinjectors and on-body injectors may continue to allow drug to pass through the needle or cannula even though a component of the device (e.g., injector) has become detached from the patient and the needle or cannula no longer is inserted into the patient. This has several consequences. First, the patient does not receive the full dose of the drug, which may have a negative effect on the patient. Second, the patient may not be aware of the fact that the full dose of the drug has not been delivered, leaving the patient with the false impression that the entire dose has been delivered when it has not. Third, even if the patient is aware of the fact that the full dose has not been delivered, the patient may be unable to determine just how much of the dose was delivered. Conversely, the patient may not be able to determine how much of the dose was not delivered.

As set forth in more detail below, the present disclosure provides an improved drug delivery device embodying advantageous alternatives to the conventional devices and methods.

SUMMARY

According to an aspect of the disclosure, a drug delivery device can include a reservoir, a cannula, a drive, a lock, a housing and a proximity sensor. The reservoir can include a bore having a first end and a second end, and a plunger assembly including a plunger moveable within the bore between the first and second ends. The cannula can have an operational state wherein the cannula is connected in fluid communication with the reservoir. The drive can be coupled to the plunger assembly to move the plunger between the first and second ends. The lock can be configured to selectively limit movement of the plunger between the first and second ends of the reservoir The reservoir, the drive, and the lock can be disposed at least partially within the housing. The proximity sensor can be operably coupled to move relative to the housing, and can have a first sensor state wherein the proximity sensor extends from the housing and a second sensor state wherein the proximity sensor is retracted toward the housing relative to the first sensor state. The lock can limit movement of the plunger assembly when the proximity sensor is in the first sensor state.

According to a further aspect of the disclosure, a method of limiting the delivery of a drug from a drug delivery device after the drug delivery device is removed from a patient can be provided. The method can include (a) providing a drug delivery device, wherein the drug delivery device can include a reservoir, a cannula, a drive, a lock, a housing and a proximity sensor. The reservoir can include a bore having a first end and a second end, and a plunger assembly including a plunger moveable within the bore between the first and second ends. The cannula can have an operational state wherein the cannula is connected in fluid communication with the reservoir. The drive can be coupled to the plunger assembly for moving the plunger between the first and second ends. The lock can be configured to selectively limit movement of the plunger between the first and second ends of the reservoir. The reservoir, the drive, and the lock can be disposed at least partially within the housing. And the proximity sensor can be operably coupled to move relative to the housing, and can have a first sensor state wherein the proximity sensor extends from the housing and a second sensor state wherein the proximity sensor is retracted toward the housing relative to the first sensor state. The lock can limit movement of the plunger assembly when the proximity sensor is in the first sensor state. The method can further include, (b) when the drug delivery device is removed from the patient, causing the proximity sensor to occupy the first sensor state after having occupied the second sensor state. And, the method can include, (c) transmitting information from the proximity sensor to the lock to indicate that the proximity sensor has moved to the first sensor state. Finally, the sensor can include (d) causing the lock to limit movement of the plunger assembly upon receiving information that the proximity sensor is in the first sensor state.

According to another aspect of the present disclosure, a drug delivery device such as an injector can include a reservoir including a bore having a first end and a second end, and a plunger assembly including a plunger moveable within the bore between the first and second ends, and a cannula having an operational state wherein the cannula is connected in fluid communication with the reservoir. The injector also includes a spring coupled to the plunger assembly to move the plunger between the first and second ends, a lock selectively coupled to one of the plunger assembly and the spring to limit movement of the plunger between the first and second ends with the lock coupled to the one of the plunger assembly and the spring, a housing, the reservoir, spring, and lock disposed within the housing, and a proximity sensor coupled to the lock and moveable relative to the housing, the proximity sensor having a first sensor state wherein the proximity sensor extends fully from the housing and a second sensor state wherein the proximity sensor is retracted toward the housing, the lock coupled to the one of the plunger assembly and the spring with the proximity sensor in the first sensor state.

According to another aspect of the present disclosure, a drug delivery device such as an injector can include a reservoir including a bore having a first end and a second end, and a plunger assembly including a plunger moveable within the bore between the first and second ends, and a cannula having an operational state wherein the cannula is connected in fluid communication with the reservoir. The injector also includes a gas source having an operational state wherein the gas source is in fluid communication with the plunger to move the plunger between the first and second ends, a lock comprising a vent selectively coupled to the gas source to limit movement of the plunger between the first and second ends, a housing, the reservoir, gas source, and lock disposed within the housing, and a proximity sensor coupled to the lock and moveable relative to the housing, the proximity sensor having a first sensor state wherein the proximity sensor extends fully from the housing and a second sensor state wherein the proximity sensor is retracted toward the housing, the vent coupled to the gas source with the proximity sensor in the first sensor state.

According to a further aspect of the present disclosure, a drug delivery device such as an injector can include a reservoir including a bore having a first end and a second end, and a plunger assembly including a plunger moveable within the bore between the first and second ends, and a cannula having an operational state wherein the cannula is connected in fluid communication with the reservoir. The injector also includes a spring coupled to the plunger assembly to move the plunger between the first and second ends, an indicator selectively mechanically coupled to the plunger assembly, a housing, the reservoir, spring, and indicator at least partially disposed within the housing, and a proximity sensor coupled to the indicator and moveable relative to the housing, the proximity sensor having a first sensor state wherein the proximity sensor extends fully from the housing and a second sensor state wherein the proximity sensor is retracted toward the housing, the indicator coupled to the plunger assembly with the proximity sensor in the second sensor state and the indicator decoupled from the plunger assembly with the proximity sensor in the first sensor state.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

GENERAL DESCRIPTION

Figure 1:
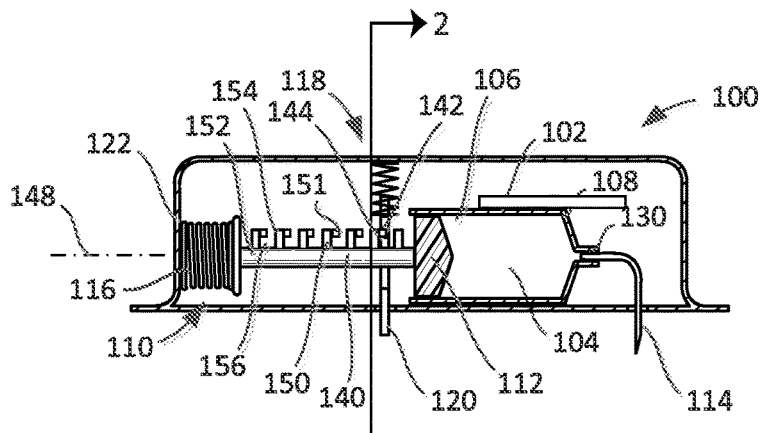
FIG. 1 is a cross-sectional view of an embodiment of a drug delivery device with a sliding lock that cooperates with a plunger arm and a proximity sensor in a first, off-body state.

A drug delivery device, in the form of an injector, may include various systems for limiting the delivery of a medical fluid or drug product in case of movement of (e.g., removal of) the injector relative to a patient as determined by a proximity sensor. The drug delivery system may in the alternative or in addition include systems for indicating the amount of medical fluid or drug product delivered (or not delivered) in the case of movement of (e.g., removal of) the injector relative to the patient as determined by the proximity sensor. The injector may be, for example, an on-body injector or a hand-held autoinjector. The injector may be used with one of a variety of medical fluids or drug products.

In one embodiment, an injector comprises a reservoir including a bore having a first end and a second end, and a plunger assembly including a plunger moveable within the bore between the first and second ends. The injector further comprises a cannula having an operational state wherein the cannula is connected in fluid communication with the reservoir, and a spring coupled to the plunger assembly to move the plunger between the first and second ends. The injector also comprises a lock selectively coupled to one of the plunger assembly and the spring to limit movement of the plunger between the first and second ends with the lock coupled to the one of the plunger assembly and the spring, a housing, the reservoir, spring, and lock disposed within the housing, and a proximity sensor coupled to the lock and moveable relative to the housing, the proximity sensor having a first sensor state wherein the proximity sensor extends fully from the housing and a second sensor state wherein the proximity sensor is retracted toward the housing, the lock coupled to the one of the plunger assembly and the spring with the proximity sensor in the first sensor state.

According to another embodiment, the plunger assembly includes a plunger arm attached to the plunger, the lock has a wall that abuts the plunger arm to limit movement of the plunger when the lock is coupled to the plunger assembly, and the proximity sensor is coupled to the wall, where the wall abuts the plunger arm with the proximity sensor in the first sensor state and the wall is spaced from the plunger arm with the proximity sensor in the second sensor state.

According to another embodiment, the plunger arm has at least one shoulder formed thereon, and the wall abuts the at least one shoulder of the plunger arm to limit movement of the plunger when the lock is coupled to the plunger assembly.

According to another embodiment, the injector further comprises a plate disposed at least partially within the housing and coupled to the housing to translate relative to the plunger arm, the plate having a first end that defines the wall of the lock and a second end that defines the proximity sensor.

According to another embodiment, the injector further comprises a lever having a first end disposed within the housing and defining the wall of the lock, and a second end disposable outside the housing and defining the proximity sensor.

According to another embodiment, the lock has a wall that abuts the spring to limit movement of the plunger when the lock is coupled to the spring, and the proximity sensor is attached to the wall, where the wall abuts the spring with the proximity sensor in the first sensor state and the wall is spaced from the spring with the proximity sensor in the second sensor state.

According to another embodiment, the injector further comprises a plate disposed at least partially within the housing and coupled to the housing to translate relative to the spring, the plate having a first end that defines the wall of the lock and a second end that defines the proximity sensor.

According to another embodiment, the injector further comprises a lever having a first end disposed within the housing and defining the wall of the lock, and a second end disposable outside the housing and defining the proximity sensor.

According to another embodiment, the injector further comprises a spring coupled to the proximity sensor, the spring biasing the proximity sensor toward the first sensor state.

According to another embodiment, the lock is reversibly coupled to the one of the plunger assembly and the spring.

According to another embodiment, the lock is irreversibly coupled to the one of the plunger assembly and the spring.

According to another embodiment, the proximity sensor has a third sensor state wherein the proximity sensor is retracted toward the housing, the lock being coupled to the one of the plunger assembly and the spring with the proximity sensor in the third sensor state, the lock being reversibly coupled to the one of the plunger assembly and the spring with the sensor occupying the third sensor state subsequent to occupying the second sensor state, and the lock being irreversibly coupled to the one of the plunger assembly and the spring with the sensor occupying the first sensor state subsequent to occupying one of the second and third sensor states.

According to another embodiment, the lock prevents movement of the plunger between first and second ends with the lock coupled to the one of the plunger assembly and the spring.

According to another embodiment, the lock limits movement of the plunger between first and second ends with the lock coupled to the one of the plunger assembly and the spring.

According to another embodiment, the injector is a handheld autoinjector, the injector comprising a needle shield that defines the proximity sensor.

According to another embodiment, the injector is an on-body injector, the injector comprising a surface having adhesive applied thereto to attach the injector to a body of a patient.

According to a further embodiment, an injector comprises a reservoir including a bore having a first end and a second end, and a plunger assembly including a plunger moveable within the bore between the first and second ends, a cannula having an operational state wherein the cannula is connected in fluid communication with the reservoir, and a gas source having an operational state wherein the gas source is in fluid communication with the plunger to move the plunger between the first and second ends. The injector further comprises a lock comprising a vent selectively coupled to the gas source to limit movement of the plunger between the first and second ends, a housing, the reservoir, gas source, and lock disposed within the housing, and a proximity sensor coupled to the lock and moveable relative to the housing, the proximity sensor having a first sensor state wherein the proximity sensor extends fully from the housing and a second sensor state wherein the proximity sensor is retracted toward the housing, the vent coupled to the gas source with the proximity sensor in the first sensor state.

According to another embodiment, the gas source is a pressurized container of gas.

According to another embodiment, the gas source is a container of a material capable of a phase change from liquid to gas or solid to gas.

According to another embodiment, the vent comprises a seal.

According to another embodiment, the vent comprises a piercable septum.

According to a still further embodiment, an injector comprises a reservoir including a bore having a first end and a second end, and a plunger assembly including a plunger moveable within the bore between the first and second ends, a cannula having an operational state wherein the cannula is connected in fluid communication with the reservoir, and a spring coupled to the plunger assembly to move the plunger between the first and second ends. The injector further comprises an indicator selectively mechanically coupled to the plunger assembly, a housing, the reservoir, spring, and indicator at least partially disposed within the housing, and a proximity sensor coupled to the indicator and moveable relative to the housing, the proximity sensor having a first sensor state wherein the proximity sensor extends fully from the housing and a second sensor state wherein the proximity sensor is retracted toward the housing, the indicator coupled to the plunger assembly with the proximity sensor in the second sensor state and the indicator decoupled from the plunger assembly with the proximity sensor in the first sensor state.

According to another embodiment, the plunger assembly comprises a plunger arm attached to the plunger, the indicator being mechanically coupled to the plunger arm through a gear train having at least one gear that is moveable into and out of engagement, and the proximity sensor is coupled to the at least one gear to move the at least one gear out of engagement and decouple the indicator from the plunger arm with the proximity sensor in the first sensor state.

DETAILED DESCRIPTION

Figure 2:
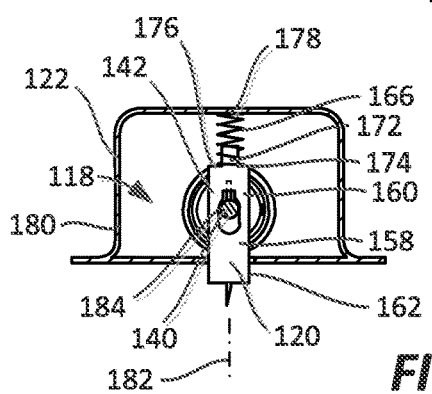
FIG. 2 is a cross-sectional view of the embodiment of FIG. 1 taken along line 2-2, with the proximity sensor in the first, off-body state.
Figure 3:
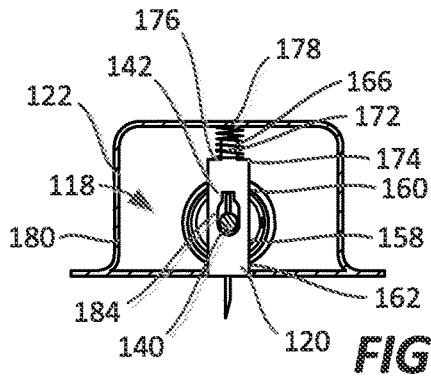
FIG. 3 is a cross-sectional view of the embodiment of FIG. 1 taken along line 2-2, with the proximity sensor in a second, on-body state.

Turning now to FIGS. 1-3, a drug delivery device such as an injector 100 includes a reservoir 102, a plunger assembly 110, a cannula 114, and a drive 116. The reservoir 102 includes a bore 104 having a first end 106 and a second end 108. The plunger assembly 110 includes a plunger 112 moveable within the bore 104 of the reservoir 102 between the first and second ends 106, 108. The cannula 114 includes an operational state wherein the cannula 114 is connected in fluid communication with the reservoir 102. The drive 116, in the form of a spring, is coupled to the plunger assembly 110 to move the plunger 112 between the first and second ends 106, 108.

Figure 9:
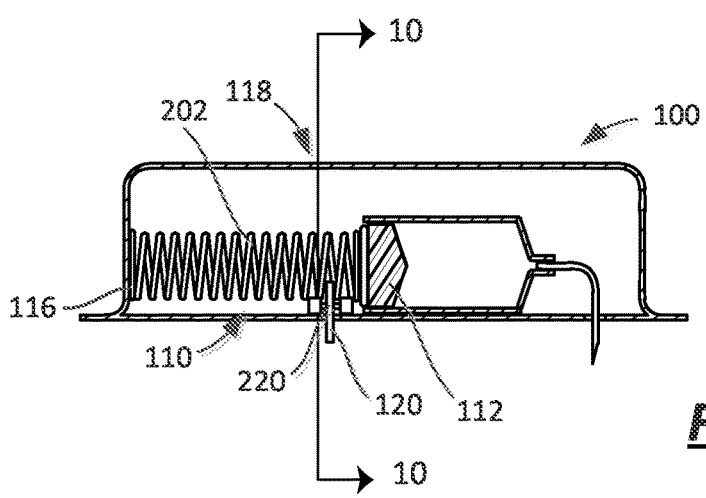
FIG. 9 is a cross-sectional view of an embodiment of a drug delivery device with a pivoting lock that cooperates with a spring and a proximity sensor in a first, off-body state.
Figure 10:
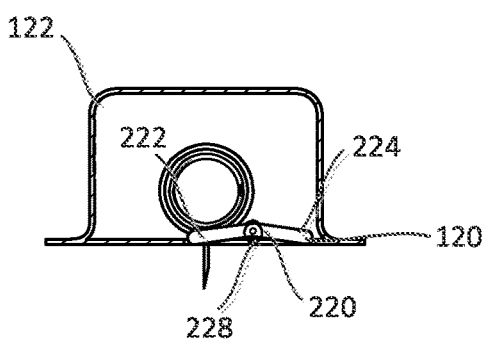
FIG. 10 is a cross-sectional view of the embodiment of FIG. 9 taken along line 10-10, with the proximity sensor in a second, on-body state.
Figure 11:
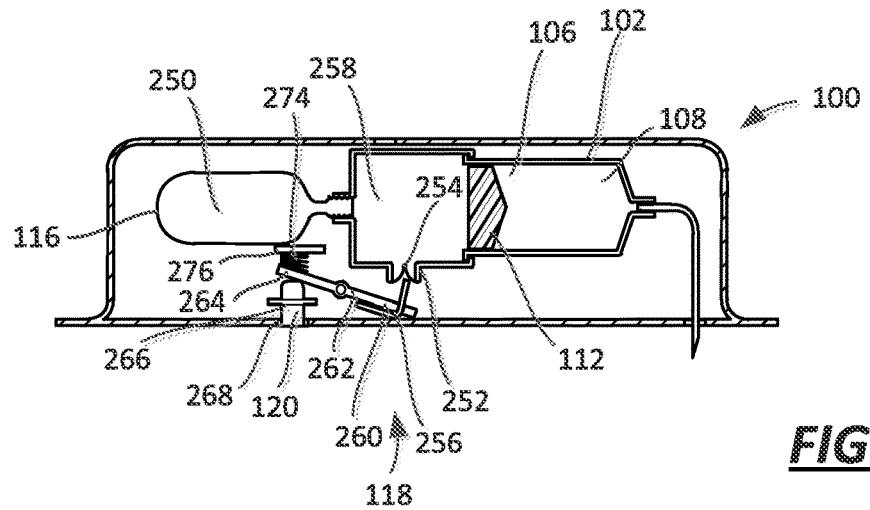
FIG. 11 is a cross-sectional view of an embodiment of a drug delivery device with a lock including a vent and a proximity sensor in a second, on-body state.
Figure 12:
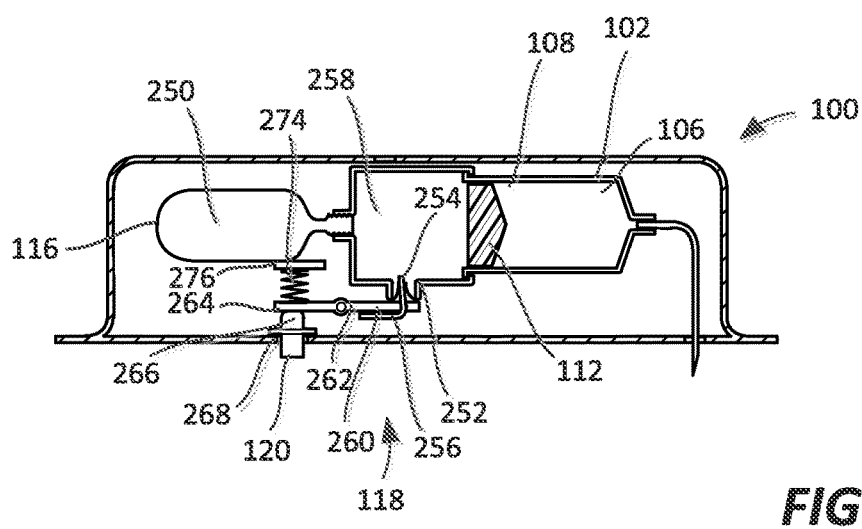
FIG. 12 is a cross-sectional view of the embodiment of FIG. 11 with the proximity sensor in a first, off-body state.

According to the embodiments illustrated in FIGS. 1-12, the injector 100 is also provided with a lock 118 selectively coupled to one of the plunger assembly 110 and the drive 116 to limit movement of the plunger 112 between the first and second ends 106, 108 of the bore 104. For example, the lock 118 may be coupled to the one of the plunger assembly 110 and the spring 116. See, e.g., FIGS. 1-10. Another embodiment of the lock 118 is illustrated in FIGS. 11 and 12.

The injector 100 includes a proximity sensor 120 coupled to the lock 118 and moveable relative to a housing 122 in which the reservoir 102, spring 116, and lock 118 are disposed. The proximity sensor 120 has a first sensor state (or position) wherein the proximity sensor 120 extends (e.g., extends fully) from the housing 122 (see, e.g., FIGS. 1 and 2) and a second sensor state (or position) wherein the proximity sensor 120 is retracted toward and into the housing 122 relative to the first sensor state (see, e.g., FIG. 3). The lock 118 is coupled to the one of the plunger assembly 110 and the spring 116 with the proximity sensor 120 in the first sensor state so as to limit or prevent movement of the plunger 112.

In certain embodiments, the reservoir 102 may be in the form of a pre-filled syringe, in which case the cannula 114 may be in the form of a needle fixedly or securely attached to a hub 130 at the second end 108 of the reservoir 102. See, FIG. 1. According to other embodiments, the reservoir 102 may be pre-filled, but the cannula 114 may be moveable relative to the hub 130 of the reservoir 102. In some embodiments, the hub 130 can include a septum such that the cannula 114 can be moved in the direction of the hub 130 to pierce the septum in the operational state. In certain embodiments, an assembly may be disposed between the cannula 114 and the hub 130 to dispose the cannula 114 into fluid connection with the hub 130 in the operational state, which assembly may also insert the cannula 114 into the patient. In some embodiments, a barrier may be disposed about the end of the cannula 114 that pierces the septum to preserve the sterility at the junction between the cannula 114 and the septum. In some embodiments, the cannula 114 either may be fixedly or securely attached or may be moveable relative to the reservoir 102 (more particularly, the hub 130), but the reservoir 102 may not be pre-filled.

As illustrated in FIG. 1, the plunger assembly 110 may include a plunger arm 140 attached to the plunger 112. The lock 118 has a wall 142 that abuts the plunger arm 140 to limit movement of the plunger 112 when the lock 118 is coupled to the plunger assembly 110. The proximity sensor 120 is coupled to the wall 142 (as illustrated, the sensor 120 is integral, or one piece, with the wall 142), such that the wall 142 abuts the plunger arm 140 with the proximity sensor 120 in the first sensor state (FIGS. 1 and 2) and the wall 142 is spaced from the plunger arm 140 with the proximity sensor 120 in the second sensor state (FIG. 3).

In some embodiments, the plunger arm 140 may have at least one shoulder 144 (FIG. 1) formed thereon, and the wall 142 abuts the at least one shoulder 144 of the plunger arm 140 to limit and/or prevent movement of the plunger 112 when the lock 118 is coupled to the plunger assembly 110. As illustrated in FIG. 1, the plunger arm 140 has a section of its length (i.e., a dimension of the plunger arm 140 extending in a direction along a longitudinal axis 148 of the plunger arm 140) that has at least one feature 150 that defines the at least one shoulder 144. For example, the plunger arm 140 may include a shaft 152 to which is attached one or more features 150 that include protrusions 154 (e.g., teeth). In some embodiments, the protrusions 154 can be formed integrally (as one piece) with the shaft 152. Spaces or notches 156 between adjacent protrusions 154 permit the wall 142 to be disposed between adjacent protrusions 154, with the protrusion 154 positioned furthest longitudinally from the plunger 112 defining the shoulder 144 along a surface of the protrusion 154 that extends perpendicularly to the axis 148. It will be recognized that the features 150 of the embodiment illustrated in FIGS. 1-3 may also be described as one or more spaces or notches 156 formed in the plunger arm 140, the spaces or notches 156 being bounded by the material of the plunger arm 140 previously described as shaft 152 and protrusions 154. These are equivalent descriptions for the disclosed subject matter.

As noted above, the lock 118 includes a wall 142 that fits in the spaces or notches 156 thereby coupling the lock 118 to the plunger assembly 110. According to the embodiment illustrated in FIGS. 1-3, the injector 100 includes a plate 158 disposed at least partially within the housing 122 and coupled to the housing 122 to translate relative to the plunger arm 140. The plate 158 may have a first end 160 that defines the wall 142 of the lock 118 and a second end 162 that defines the proximity sensor 120. See FIGS. 2 and 3. While the wall 142 has been described as being part of the plate 158, which is depicted in FIGS. 2 and 3, for example, as a generally planar structure, this is merely an example. The wall 142 of the lock 118 could also be defined by part of a pin, a fork, or any other component not expressly depicted but capable of serving the intended purpose.

In some embodiments, the injector 100 may include a spring 166 coupled to the proximity sensor 120 (via the plate 158), the spring 166 biasing the proximity sensor 120 (again, via the plate 158) toward the first sensor state. In certain embodiments, the second end 160 may include a guide 172 about which the spring 166 is disposed, a first end 174 of the spring 166 abutting a shoulder 176 of the plate 158 and a second end 178 abutting an interior surface 180 of the housing 122. While a coil spring 166 is illustrated, any of a number of different biasing elements may be used, which biasing elements may bias the first end 162 of the plate 158 outwardly from the housing 122.

In some embodiments, the injector 100 may include guides attached to the housing 122 that prevent the plate 158 from other than translational movement along a line of motion 182. For example, a guide may be disposed on either side of the plate (i.e., to the right or the left of the plate 158 as illustrated in FIG. 2) to prevent lateral movement relative to the line of motion 182.

Disposed between the first and second ends 160, 162 of the plate 158 is an aperture 184. While the aperture 184 appears to be closer to the second end 160 of the plate 158 than the first end 162, other arrangements are possible. Furthermore, while the aperture 184 appears to be fully surrounded by the plate 158, such that the entire circumference of the aperture 184 is defined by the plate 158, it is also possible that at least a section of the aperture 184 is not surrounded by the plate 158 and thus the plate 158 only partially defines the circumference of the aperture 184. Furthermore, while the circumference of the aperture 184 appears oblong or keyhole in shape in FIG. 2, the aperture 184 is not limited to any particular shape.

As illustrated in FIGS. 1 and 2, when the injector 100 is not disposed on the surface of the patient's skin, the proximity sensor 120 extends from the housing 122 as a consequence of the force applied to the plate 158 by the spring 166. See FIG. 2. In turn, the plate 158 is positioned relative to the plunger assembly 110, and in particular the plunger arm 140, such that the plate 158 resides within one of the spaces or notches 156. Compare FIGS. 1 and 2. When the injector 100 is disposed on the surface of the patient's skin, the proximity sensor 120 is moved into the housing 122 against the bias of the spring 166. As a consequence, the plate 158 is moved into a position where the aperture 184 is aligned with the plunger arm 140, such that the plate 158 no longer resides within one of the spaces or notches 156. See FIG. 3. This permits movement of the plunger arm 140 and associated plunger 112 as a consequence of the force applied to the plunger arm 140 by the spring 116.

During the motion of the plunger arm 140 toward the right relative to the orientation of FIG. 1, the injector 100 may become detached or displaced from the patient's skin. In such a case, the plate 158 would be permitted to move under bias of the spring 166 such that the aperture 184 is no longer aligned with the plunger arm 140, and instead the plate 158 becomes disposed within one of the spaces or notches 156. In this version, the spring 166 transmits information to the lock 118 in the form of a mechanical force indicative of the position of the plate 158 and proximity sensor 120. This force can cause engagement between the plate 158 and one of the protrusions 154 that would prevent further motion of the plunger arm 140 at the urging of the spring 116, and would limit the amount of medical fluid or drug product ejected from the reservoir 102. That is, according to certain embodiments, engagement between the plate 158 and a protrusion may prevent any further medical fluid or drug product from passing through and out of the cannula 114. According to other embodiments, the plunger arm 140 and associated plunger 112 may travel some distance after the plate 158 becomes disposed within a space or notch 156 but before the plate 158 engages a protrusion 154, such that a limited amount of medical fluid or drug product may pass out of the reservoir through the cannula 114 even after activation of the lock 118. It will be recognized that by limiting the amount of medical fluid or drug product ejected from the reservoir 102, while arresting the overall motion of the plunger 112, significant advantages may still be obtained.

It is not necessary that the lock 118 and proximity sensor 120 be defined by a translating plate, such as is illustrated in FIGS. 1-3. The embodiment illustrated in FIGS. 4 and 5 includes a different structure that defines both a lock 118 and a proximity sensor 120. Because many of the structures of the embodiment of the injector illustrated in FIGS. 4 and 5 are identical to those of the embodiment of FIGS. 1-3, like elements have like reference numerals.

Figure 4:
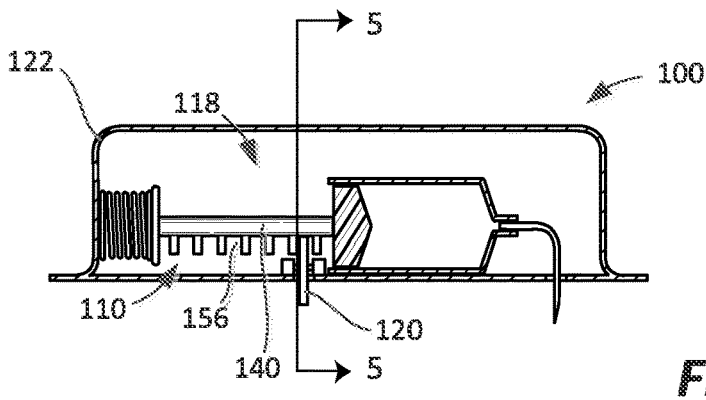
FIG. 4 is a cross-sectional view of another embodiment of a drug delivery device with a pivoting lock that cooperates with a plunger arm and a proximity sensor in a first, off-body state.
Figure 5:
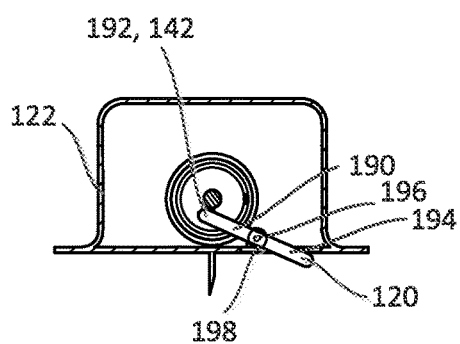
FIG. 5 is a cross-sectional view of the embodiment of FIG. 4 taken along line 5-5, with the proximity sensor in the first, off-body state.

The structure of the embodiment illustrated in FIGS. 4 and 5 that defines both the lock 118 and the proximity sensor 120 is a lever 190. As shown in FIG. 5, the lever 190 has a first end 192 disposed within the housing 122 and defining the wall 142 of the lock 118, and a second end 194 disposable outside the housing 122 and defining the proximity sensor 120. Disposed between the first and second ends 192, 194 is a pivot 196 that may be attached to the housing 122.

The injector 100 may include a spring 198 coupled to the proximity sensor 120, the spring 198 biasing the proximity sensor 120 (lever 190) toward the first sensor state with the sensor 120 extending from the housing 120. As illustrated, the spring 198 is a torsion spring that is disposed at the pivot 196 and that applies a force to the lever 190 to one or the other side of the lever 190 to bias the lever 190, and thus the sensor 120, toward the first sensor state (i.e., in a clockwise direction relative to the orientation of FIG. 5). It will be recognized that other biasing elements may be used instead. For example, a compression spring may be disposed between the first end 192 of the lever 190 and the housing 122 to urge the lever 190, and thus the sensor 120, toward the first sensor state.

Some change in orientation of the elements of the injector 100 may be required to utilize the lever 190. Because the motion of the second end 194 of the lever 190 into the housing 122 causes the first end 192 to move counter-clockwise, the orientation of the plunger arm 140, and the spaces or notches 156 on the plunger arm 140, may be the reverse of that illustrated in the embodiment of FIGS. 1-3. The spaces or notches 156 may be positioned below the plunger arm 140, as depicted in FIG. 4. In this fashion, movement of the lever 190 caused by the motion of the second end 194 upon application of the injector 100 to the patient's skin would cause the first end 192 to move away from the plunger arm 140 and out of its respective space or notch 156. And upon removal of the injector 100 from the patient's skin, whether deliberate or not, the spring 198 would cause the first end 192 of the lever 190 to move toward the plunger arm 140 and into a respective space or notch 156 to lock the device. In this version, the spring 198 transmits information to the lock 118 in the form of a mechanical force indicative of the position of the lever 190 and thus the proximity sensor 120.

Figure 6:
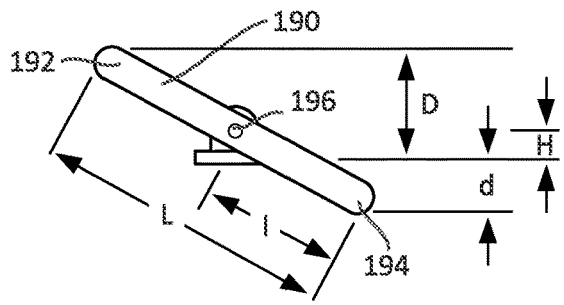
FIG. 6 is a diagram relating the motion of the ends of the lever of the embodiment illustrated in FIGS. 4 and 5.

One advantage of the lever 190 is that it can permit a magnification of the travel of the second end 194, which in turn can increase the sensitivity of the proximity sensor 120. In particular, as illustrated in FIG. 6, the second end 194 moves a distance d relative to the surface of the housing 122 (for purposes of this discussion, this surface is also the patient contact surface). The first end 192 in turn moves a distance D relative to the same surface of the housing 122. These distances (d, D) are related to a length L of the lever 190, a length l of the lever 190 to the second end 194 and the offset H of the pivot 196 relative to the surface of the housing 122. If the length l is one-third of the length L, then changes in the distance d will result in changes approximately twice as large for the distance D (assuming a relatively small offset H). As long as length l is less than half of length L, an increased sensitivity to motion will be realized.

The sensitivity of the embodiment utilizing a lever 190 may also be influenced by changes in the shape of the lever 190. The lever 190 illustrated in FIGS. 4-6 is relatively straight. Alternatively, the lever 190 may be shaped with a bend between the two ends 192, 194 to change the relationship between the movement of the second end 194 to the first end 192.

While the embodiments of FIGS. 1-3 and 4-6 have been illustrated with a single structure (plate 158, lever 190) defining both the lock 118 and the proximity sensor 120, other embodiments may not be so limited. For example, both the lock 118 and the sensor 120 may each be defined by a translating plate, similar to the plate 158, except that the first plate that defines the lock 118 may be disposed in a first region of the injector 100 and the second plate that defines the sensor 120 may be disposed in a second region of the injector 100 spatially removed from the first region. The second plate that defines the sensor 120 may be coupled to the first plate that the defines the lock 118 by a lever or other mechanical system disposed within the housing. A pivot for the lever coupling the sensor 120 to the lock 118 may be selected to provide greater sensitivity that may be possible if a single structure defined both lock 118 and sensor 120. In addition, a lever may permit the sensor 120 to be disposed closer to the cannula 114 while the lock 118 is disposed proximate to the plunger arm 140, because the lock 118 and the sensor 120 are not defined by a single structure.

In further embodiments, other structures or assemblies of structures may be used to transform motion of the sensor 120 into motion of the lock 118. The foregoing example is simply one possible embodiment of a class of embodiments, individual examples of which may permit greater sensitivity while not necessarily permitting the lock 118 and the sensor 120 to be disposed in spatially remote sections of the injector, and vice versa. Further, embodiments may provide other functions in addition or in substitution for those previously mentioned. For example, an intermediate structure or assembly may couple a sensor 120 moving in a first direction to a lock 118 moving in a second direction, which direction may be different from the first (i.e., the sensor 120 may travel along a first line of motion while the lock 118 moves along a second line of motion that is at right angles to the first line of motion).

As noted above, the lock 118 may be coupled to one of the plunger assembly 110 and the spring 116. As illustrated in FIGS. 7-10, the lock 118 may be coupled to the spring 116 instead of the plunger assembly 110.

According to this embodiment, the plunger assembly 110 may or may not include a plunger arm 140. As illustrated in FIGS. 7-10, the plunger assembly 110 does not include a plunger arm 140, but the spring 116 acts directly against the plunger 112, the force applied by the spring 116 causing motion of the plunger 112. It will be recognized that the embodiments of the lock 118 described below would work equally as well if the spring 116 applied its force to an intermediate structure, such as a plunger arm 140, instead of directly to the plunger 112.

Figure 7:
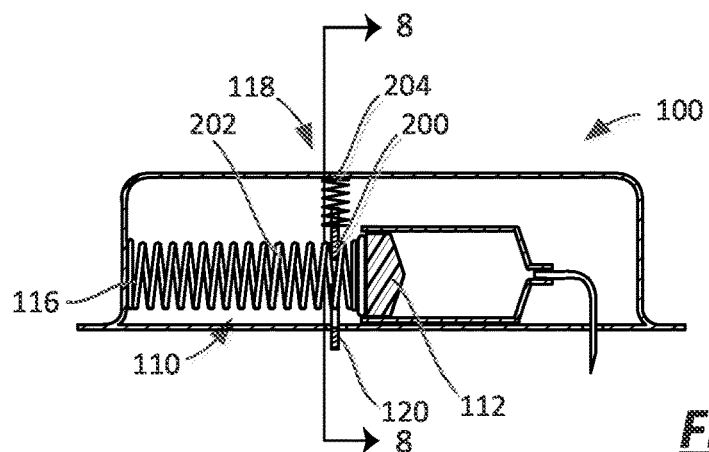
FIG. 7 is a cross-sectional view of an embodiment of a drug delivery device with a sliding lock that cooperates with a spring and a proximity sensor in a first, off-body state.

According to the embodiment illustrated in FIG. 7, the lock 118 has a wall 200 that abuts the spring 116 to limit movement of the plunger 112 when the lock 118 is coupled to the spring 116. In some embodiments, as illustrated, the spring 116 may be a coil spring, and the wall 200 may be disposed between adjacent coils 202 of the spring 116 to limit the force applied to the plunger 112. The proximity sensor 120 is attached to the wall 200, and the wall 200 abuts the spring 116 with the proximity sensor 120 in the first sensor state and the wall 200 is spaced from the spring 116 with the proximity sensor 120 in the second sensor state. In some embodiments, the injector may include a spring 204 coupled to the proximity sensor 120, the spring 204 biasing the proximity sensor 120 toward the first sensor state.

Figure 8:
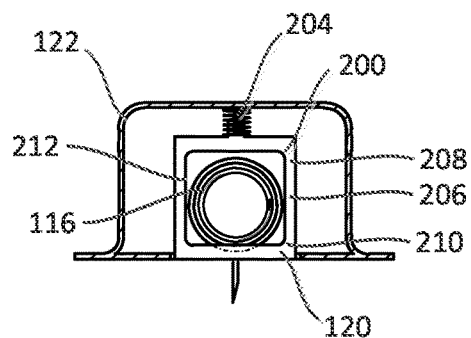
FIG. 8 is a cross-sectional view of the embodiment of FIG. 7 taken along line 8-8, with the proximity sensor in a second, on-body state.

The embodiment illustrated in FIGS. 7 and 8 may include a plate 206 that defines the wall 200. The plate 206 may be disposed at least partially within the housing 122 and coupled to the housing 122 to translate relative to the spring 116. The plate 206 may have a first end 208 that defines the wall 200 of the lock 118 and a second end 210 that defines the proximity sensor 120. In some embodiments, the plate 206 includes an aperture 212 that is sized such that the spring 116 may pass through the plate 206 when the sensor 120 is in the second sensor state, the consequence of which would be for the spring 116 to move freely without interference from the plate 206 and exert a force against the plunger 112.

The discussion relative to the operation and configuration of the plate 158 relative to the plunger arm 140 applies with equal force relative to the operation and configuration of the plate 206 relative to the spring 116. For example, like the version in FIGS. 1-3, when the injector 100 in FIGS. 7 and 8 is removed from the patient, the spring 204 transmits information to the plate 206 of the lock 118 in the form of a mechanical force indicative of the position of the proximity sensor 120.

In some embodiments, the injector may include a lever 220, as illustrated in FIGS. 9 and 10, in substitution for the plate 206. As shown in FIG. 10, the lever 220 may have a first end 222 disposed within the housing 122 and defining the wall 200 of the lock 118. The lever 220 may also have a second end 224 disposable outside the housing 122 and defining the proximity sensor 120. This injector may also include a spring 228 coupled to the proximity sensor 120, the spring 228 biasing the proximity sensor 120 (lever 220) toward the first sensor state. For example, the spring 228 may be a torsion spring.

The discussion relative to the operation and configuration of the lever 190 relative to the plunger arm 140 applies with equal force relative to the operation and configuration of the lever 220 relative to the spring 116. For example, like the version in FIGS. 4-6, when the injector 100 in FIGS. 9 and 10 is removed from the patient, the spring 228 transmits information to the wall 200 of the lock 118 in the form of a mechanical force indicative of the position of the lever 220 and proximity sensor 120. In addition, the discussion above relative to the lock 118 and the sensor 120 being defined by a single structure or by separate structures coupled by one or more intermediate structures or assemblies of structures applies with equal force regarding the embodiments illustrated in FIGS. 7-10 as it did relative to the embodiments illustrated in FIGS. 1-6.

According to some embodiments, the lock 118 may be reversibly coupled to the one of the plunger assembly 110 and the spring 116. For example, if the injector 100 is removed from the patient's skin during administration, the lock 118 would limit or prevent further administration of the medical fluid or drug product. But, in embodiments where the lock 118 is reversible, the lock 118 may be unlocked, or decoupled, if the proximity sensor 120 determines that the injector 100 has been replaced against the patient's skin. In other embodiments, the lock 118 may be irreversibly coupled to the one of the plunger assembly 110 and the spring 116. Such embodiments would prevent the injector 100 from operating even if the injector 100 was re-positioned against the patient's skin. In some embodiments, the decision to make the lock 118 reversible or irreversible may be selected by the patient or caregiver using the delivery device.

One example of an irreversible lock 118 is illustrated in FIG. 1, wherein all but one of the features 150 extending up from the plunger arm 140 can include transverse teeth 151 extending into spaces or notches 156 between the features 150. In the version of FIG. 1, all of the features 150 include a tooth 151 except for the feature 150 located in closest proximity to the plunger 112. So configured, before the injector 100 is ever operated, the lock 118 resides in the space or notch 156 disposed between the plunger 112 and the adjacent toothless feature 150. Upon the injector 100 being positioned against a patient's skin, the proximity sensor 120 and lock 118 move into the injector 100 to allow the plunger assembly 110 to drive the plunger 112 and administer drug to the patient. This causes the plunger arm 140 to move to the right relative to the orientation of FIG. 1. Then, once the injector 100 is removed from the patient's skin, the spring 166 biases the lock 118 and proximity sensor 120 back out of the injector 100 and into the position illustrated in FIG. 1, for example. Here, the lock 118 would be positioned in a space or notch 156 between two features 150, one of which includes a tooth 151. The tooth 151 resides above the lock 118, or in a recess formed in the lock 118, for example, such that a bottom surface of the tooth 151 engages an upward facing surface of the lock 118, thereby preventing the lock 118 and proximity sensor 120 from moving back up into the injector 100. While FIG. 1 illustrates the features 150 as having the teeth 151, this would only apply to those injectors 100 where the lock 118 is irreversible. For a reversible lock 118, the injector 100 would not include the teeth 151.

Some embodiments of the injector 100 may have a lock 118 that is reversibly coupled and irreversibly coupled to one of the plunger assembly 110 and the spring 116 according to the state of the proximity sensor 120. For example, the proximity sensor 120 may have a third sensor state wherein the proximity sensor 120 is retracted toward the housing relative to the first sensor state but not as far as the second sensor state. In some embodiments, the third sensor state can be considered an intermediate state between the first and second sensor states. With the proximity sensor 120 in the third sensor state, the lock 118 can be coupled to the one of the plunger assembly 110 and the spring 116 to limit or prevent further movement of the plunger 112. Further, the lock 118 may be reversibly coupled to the one of the plunger assembly 110 and the spring 116 with the proximity sensor 120 in the third sensor state subsequent to occupying the second sensor state. And, the lock 118 can be irreversibly coupled to the one of the plunger assembly 110 and the spring 116 with the proximity sensor 120 in the first sensor state subsequent to occupying one of the second and third sensor states.

To illustrate the foregoing, consider the following example. A patient applies the device to his or her skin. As a consequence, the proximity sensor 120 is disposed wholly or partially in the housing 120. As a further consequence, the lock 118 is disengaged or uncoupled from the plunger assembly 110 or the spring 116, and the device begins injecting the medical fluid or drug product into the patient.

At a time thereafter, but before the full dose has been administered, the delivery device may be disturbed, causing a separation of the device from the patient's skin, as determined by the proximity sensor 120. This disturbance may cause the cannula 114 to only shallowly penetrate the patient's skin, but may not separate the injector 100 from the patient's skin to such a degree that the cannula 114 is completely removed or the sterility of the access site is compromised. In such a circumstance, the delivery of the medical fluid or drug product may be interrupted by the coupling of the lock 118 with the plunger assembly 110 or the spring 116 to prevent medical fluid or drug product leakage that may occur because of shallow cannula 114 penetration. But, this coupling is reversible so that an application of force that moves the cannula 114 back to its proper depth, as determined by the proximity sensor 120, will cause the lock 118 to decouple from the plunger assembly 110 or spring 116, thereby re-starting administration of the medical fluid or drug product.

By having a reversible coupling, the medical fluid or drug product remaining in the reservoir 102 can be successfully delivered and would not end up being treated as waste. Consequently, reversible coupling of the lock 118 to the plunger assembly 110 or the spring 116 would provide an opportunity to save a dose in the event of a minor disturbance or use error. Additionally, this may provide a higher success rate on challenging anatomies by allowing applied pressure to fix or correct an "error" state and permit delivery to resume.

If, however, the delivery device becomes disturbed to such a degree that the cannula 114 is completely removed from the patient (for example, the device falls completely off the patient) before the full dose has been administered, then it may be undesirable to permit the patient or caregiver to reapply the injector 100 to the patient. Consequently, to reduce the likelihood that the patient or caregiver would attempt to reapply the injector 100, the lock 118 may irreversibly couple to the plunger assembly 110 or spring 116 to prevent the injector 100 from any further drug delivery.

To illustrate this concept, consider an embodiment where insertion of the cannula 114 to a depth of 6 mm is preferred and a depth of 3 mm does not cause significant leakage—the 3 mm depth may be referred to as a delivery continuation threshold, and may represent the point, degree or level under which continued delivery presents an unacceptable risk of leakage or improper administration. When the injector 100 is applied and the proximity sensor 120 is in its fully retracted state, this may correspond to a state for the cannula 114 where the cannula 114 is inserted to a depth of 6 mm. If the injector 100 is disturbed, and the sensor 120 moves to a state where it is not fully retracted or fully extended corresponding to a cannula depth of 3 mm (e.g., the sensor 120 extends 3 mm from the housing 122), then the injector 100 may permit continued injection of the medical fluid or drug product. However, if the sensor 120 moves to a state corresponding to cannula depth of 2 mm (e.g., the sensor 120 extends 4 mm from the housing 122), then the injector 100 may reversibly limit injection of the medical fluid or drug product by reversibly coupling the lock 118 to one of the plunger assembly 110 and the spring 116. If the sensor 120 then moves back to a state corresponding to a cannula depth of 3 mm (e.g., the sensor 120 extends 3 mm from the housing 122) or more, then the injection may resume.

However, if the sensor 120 moves to a state corresponding to a cannula depth of 0 mm (e.g., the sensor 120 extends 6 mm from the housing 122), then the injection would be permanently and irreversibly limited through the irreversible coupling of the lock 118 to the plunger assembly 110 or spring 116. A depth of 0 mm may be referred to as a device removal threshold, and may represent the point, degree or level at which the device has likely been compromised, removed or the cannula 114 disturbed such that further delivery/reapplication is undesirable or unsafe. A similar outcome may result where the cannula depth is not 0 mm, but some non-zero value (e.g., 1 mm). A non-zero value may be selected because even if the cannula 114 does not come completely out of the patient's skin, this may still be considered to present an unacceptable risk. Alternatively, a non-zero value may be selected so that it is not a requirement that the sensor 120 determine complete separation to fail-safe in case of a false negative for complete separation (e.g., partial interference between the housing 122 and the sensor 120).

The specifics of any particular embodiment may be influenced by, for example, the distance to which the proximity sensor 120 extends from the housing 120, the length of the cannula 114, the desired depth of the insertion of the cannula 114 into the patient, and the relationship between the depth of cannula insertion to the degree of leakage from the access site.

According to any of the foregoing embodiments, the lock 118 may limit movement of the plunger 112 between first and second ends 106, 108 so as to completely prevent movement of the plunger 112 between the first and second ends 106, 108 upon the lock 118 being coupled to the one of the plunger assembly 110 and the spring 116. Alternatively, according to any of the foregoing embodiments, the lock 118 may only limit movement of the plunger 112 between first and second ends 106, 108 without completely preventing movement of the plunger 112 between the first and second ends 106, 108 upon the lock 118 being coupled to the one of the plunger assembly 110 and the spring 116. That is, it is not a requirement of all embodiments that the engagement or coupling of the lock 118 immediately result in the complete cessation of movement of the plunger 112. In certain circumstances, the plunger 112 may continue its movement over a limited length of travel after activating the lock 118. The specific distance that the plunger 112 may travel may be known and predetermined, as a consequence of the structure and operation of the lock 118, or the distance may be approximated based on the structure and operation of the lock 118 or the tolerances in the manufacture of the injector 100. In some embodiments, any limited length of travel of the plunger 112 that is allowed after engagement or coupling of the lock 118 can occur, for example, because of the geometry of the wall 142 that forms the lock 118 and the spaces or notches 156 on the plunger arm 140. That is, in some embodiments, the spaces or notches 156 may have a dimension that is greater than a thickness or width of the wall 142. As such, it is foreseeable that in some embodiments, the plunger 112 can continue to move to the extent that the spaces or notches 156 are wider, even after the lock 118 has been engaged or coupled.

Those embodiments described above wherein the lock 118 engages or couples to the plunger assembly 110, and in particular the plunger arm 140, may be used with embodiments of an injector 100 wherein the drive 116 is not in the form of a spring. For example, any device that acts on the plunger arm 140 may be used as a drive 116 in the circumstance wherein the lock 118 engages or couples to the plunger assembly 110 to limit the injection of medical fluid or drug product from the injector 100. Where the drive 116 is not in the form of a spring, other considerations may be required when the injection is limited by interaction between the lock 118 and the drive 116.

According to another group of embodiments illustrated in FIGS. 11 and 12, the injector includes a reservoir 102 including a bore 104 having a first end 106 and a second end 108, and a plunger assembly 110 including a plunger 112 moveable within the bore 104 between the first and second ends 106, 108. The injector 100 also includes a cannula 114 having an operational state wherein the cannula 114 is connected in fluid communication with the reservoir 102.

Embodiments of the injector 100 illustrated in FIGS. 11 and 12 include a drive 116 in the form of a gas source 250 having an operational state wherein the gas source is in fluid communication with the plunger 112 to move the plunger 112 between the first and second ends 106, 108. The gas source 250 may be a container of pressurized gas. In some embodiments, the gas source 250 may be a container of a material capable of a phase change from liquid to gas or solid to gas. When activated, the gas source 250 applies positive pressure on the plunger 112 of the plunger assembly 110. In some embodiments, the gas source 250 can include a frangible seal (similar to that on a convention $CO_2$ cartridge) that is punctured by a movable needle, for example, upon activation of the injector 100. The movable needle may be operably connected to the proximity sensor 120 such that movement of the proximity sensor 120 automatically moves the needle to puncture the frangible seal and activate the gas source 250. In other embodiments, the injector 100 may include a separate button operably connected to the movable needle such that a user of the injector 100 must depress the button to move the needle and break the frangible seal on the gas source 250. In still other embodiments, the injector 100 can include a mechanical or electro-mechanical valve that opens and activates the gas source 250 upon activation of the injector 100, or some other structure capable of achieving the intended objective.

The injector 100 according to such an embodiment includes a lock 118 comprising a vent 252 selectively coupled to the gas source 250 to limit or prevent movement of the plunger 112 between the first and second ends 106, 108. When the vent 252 is opened, positive pressure from the gas source 250 can exhaust through the vent 252 instead of applying a force against the plunger 112 of the plunger assembly 110. The vent 252 could be provided by a number of different mechanisms, and may be dependent upon the manner in which the positive pressure is delivered to the plunger 112. For example, the vent 252 could be defined by a rupturable wall or a moveable seal, which could provide an irreversible or a reversible lock. According to one embodiment, the vent 252 may be in the form of a duck-bill valve.

Additionally, when the gas source 250 and vent 252 have a frangible seal or rupturable wall, the injector 100 could be considered as having an "irreversible" lock. For example, when the gas source 250 and vent 252 are opened, the vent 252 limits or prevents the positive gas pressure from being applied against the plunger assembly 110. In such an assembly, the open "vent" causes the lock to operate irreversibly because there is only a single pressure source (i.e., the gas source 250), and once its seal is broken, its contents will be expelled until it is empty, especially if a seal of the vent 252 is also broken. Therefore, if the injector 100 is removed from the patient prematurely, the gas source 250 continues to expel gas which is then exhausted out of the vent 252. Any subsequent attempt to re-administer will fail if the gas source 250 is spent.

In some embodiments, the vent 252 may include a seal 254, such as a piercable septum or a duck-bill valve, and a vent cannula 256. The vent cannula 256 pierces the seal 254 to provide an exhaust pathway out of the vent 252. The reservoir 102, gas source 250, and lock 118 may be disposed within the housing 122, while the proximity sensor 120 may be disposed in whole or in part outside of the housing 122.

According to some embodiments, the proximity sensor 120 is coupled to the lock 118 and moveable relative to the housing 122. The proximity sensor 120 has a first sensor state wherein the proximity sensor 120 extends (e.g., extends fully) from the housing 122 and a second sensor state wherein the proximity sensor 120 is retracted toward and into the housing 122 relative to the first sensor state. The vent 252 is coupled to the gas source 250 with the proximity sensor 120 in the first sensor state.

The injector 100 illustrated in FIGS. 11 and 12 includes a chamber 258 that connects the gas source 250 with the reservoir 102. The vent 252 is disposed in a wall of the chamber 258. The vent cannula 256, which may be in the form of a blunt, open-ended needle, is attached to a first end 260 of a vent lever 262. The second end 264 of the vent lever 262 is coupled to the proximity sensor 120, which may be in the form of cup-shaped button 266 that extends through an aperture 268 in a wall of the housing 122. Movement of the button 266 is transmitted by the vent lever 262 to the vent cannula 256.

The proximity sensor 120, and in particular the button 266, is biased outwardly from the housing 122 by a spring 274. The spring 274 may be disposed between a support 276 and the second end 264 of the vent lever 262, the button 266 being disposed opposite the support 276 relative to the end 264 of the vent lever 262.

In operation, with the proximity sensor 120 extended (see FIG. 12) and the gas source 250 not yet activated, the vent cannula 256 engages the seal 254 to exhaust the chamber 258. Because the gas source 250 has not yet been activated, there is no effect on the movement of the plunger 112. However, once the proximity sensor 120 retracts into the housing 122, the vent cannula 256 is moved so that the vent cannula 256 no longer interrupts the seal 254 and a positive pressure may be generated in the chamber 258 by the gas source 250. If the proximity sensor 120 extends before the full dose is administered, such as by removal of the injector 100 from the patient, the spring 274 biases the vent lever 262 such that the vent cannula 256 is moved into engagement with the seal 254, and the positive pressure in the chamber 258 is exhausted through the vent cannula 256. This decreases the pressure in the chamber 258, causing the movement of the plunger 112 to be limited, or even stopped. In this configuration, the spring 274 transmits information to the lock 118, and specifically the vent lever 262 and vent cannula 256, in the form of a mechanical force indicative of the position of the vent lever 262 and the proximity sensor 120.

The embodiment provided in FIGS. 11 and 12 is intended to be an example only. Other structures may be substituted for the seal 254, vent cannula 256, and vent lever 262. While a chamber 258 has been provided in communication with the reservoir 102 and the gas source 250, the chamber 258 may not be present in other embodiments. Additionally, in some embodiments, the cannula 114 may be an open ended needle that allows flow, as depicted in FIGS. 11 and 12, or it could just be anything that when wedged into the seal 254 prevents sealing. As such, the cannula 114 could include a thin solid rod to create a flow path around itself where the seal is poor, or a square profile might encourage even more flow. An open ended needle as depicted might be useful for puncturing a septum, for example, since a septum could be designed to reseal around the perimeter of the needle. In some embodiments, a duck-billed valve configuration may seal well when un-interrupted against pressure in one direction.

In some embodiments of the injector 100, the reservoir 102 may be visible through the wall of the housing 122. According to such embodiments, if the administration of the medical fluid or drug product is interrupted as a consequence of the operation of the lock 118, the patient or caregiver may be able to visually determine the amount of the full dose remaining in the reservoir 102. In other embodiments, the reservoir 102 may be completely enclosed within the housing 122 without provision for a window.

Figure 13:
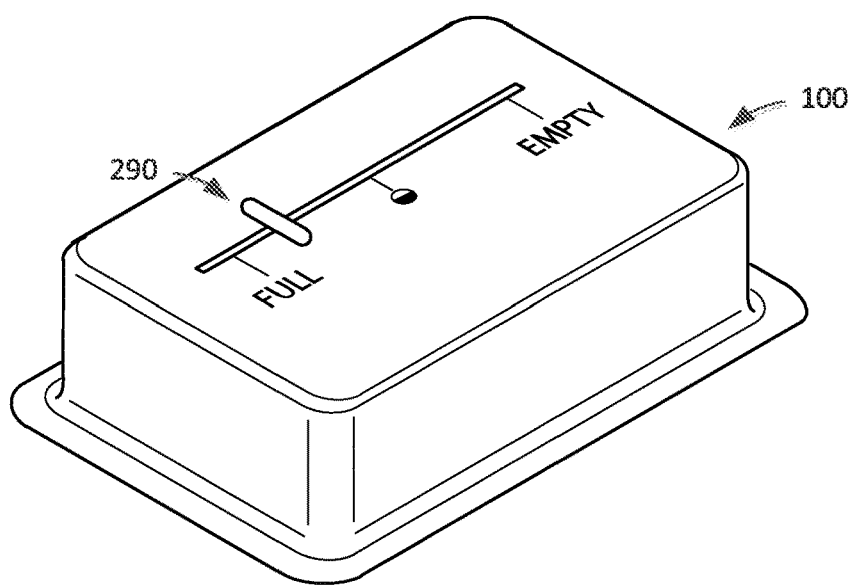
FIG. 13 is a perspective view of an injector with a fluid delivery indicator and a proximity sensor.
Figure 14:
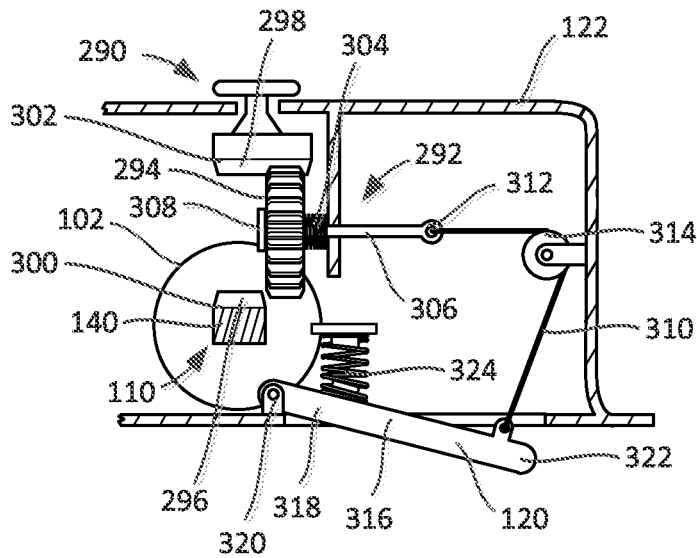
FIG. 14 is a partial cross-sectional view of the embodiment of FIG. 13 in an off-body state.
Figure 15:
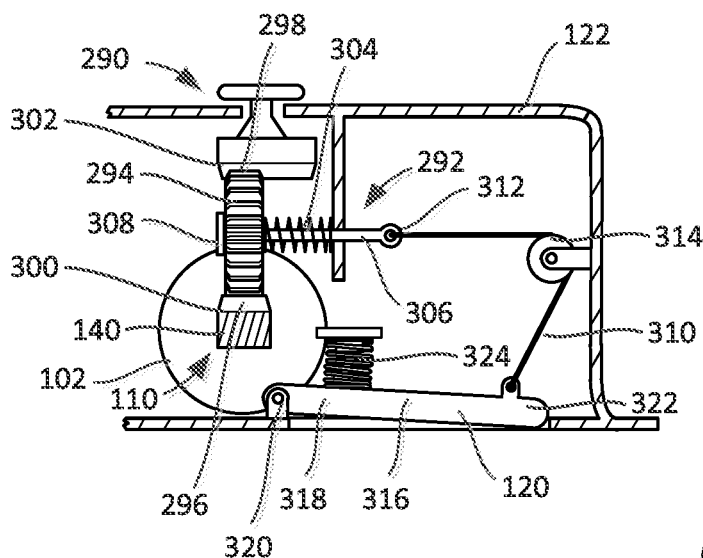
FIG. 15 is a partial cross-sectional view of the embodiment of FIG. 13 in the on-body state.

To address the situation wherein it may be difficult or impossible to visualize the reservoir 102, a third group of embodiments of the injector is illustrated in FIGS. 13-15. This group of embodiments may be used in conjunction with any of the embodiments of the injector 100 described herein. These embodiments may be used with an injector with a reservoir 102 including a bore 104 having a first end 106 and a second end 108, and a plunger assembly 110 including a plunger 112 moveable within the bore 104 between the first and second ends 106, 108. A cannula 114 may also be included, having an operational state wherein the cannula 114 is connected in fluid communication with the reservoir 102. The injector 100 further includes a spring 116 coupled to the plunger assembly 110 to move the plunger 112 between the first and second ends 106, 108. All of these structures are illustrated in FIGS. 1-3, for example, and are also applicable to the embodiment described relative to FIGS. 13-15.

In distinction to the previously described embodiments, the embodiment illustrated in FIGS. 13-15 includes an indicator 290 mechanically coupled to the plunger assembly 110. The reservoir 102, plunger arm 140, and indicator 290 are at least partially disposed within a housing 122.

A proximity sensor 120 is coupled to the indicator 290 and moveable relative to the housing 122, the proximity sensor 120 having a first sensor state wherein the proximity sensor 120 extends (e.g., extends fully) from the housing 122 and a second sensor state wherein the proximity sensor 120 is retracted toward the housing 122 relative to the first sensor state. In this version, the sensor 120 resembles the pivoting sensor 120 of FIGS. 4-6 and 9-10, and as such, it should be appreciated that the indicator 290 could be implemented into the embodiments of FIGS. 4-6 and 9-10 or any other embodiments disclosed hereinabove. That is, the indicator 290 can be combined with other injectors with locks, as disclosed. In the version of FIGS. 14 and 15, the indicator 290 is coupled to the plunger assembly 110 with the proximity sensor 120 in the second sensor state and the indicator 290 is decoupled from the plunger assembly 110 with the proximity sensor 120 in the first sensor state.

The indicator 290 mirrors the internal motion of the plunger 112 externally to the housing 122 to permit visualization. Once the proximity sensor 120 detects that the injector 100 has become detached from the patient, the indicator 290 would be decoupled from the plunger 112, such that the indicator 290 would reflect the portion of the dose remaining in the reservoir 102. According to certain embodiments, the indicator 290 may be reversibly coupled to the plunger assembly 110 so that if the injector 100 permits the injection to resume after the injector 100 is repositioned or otherwise adjusted, the indictor 290 would continue to mirror the motion of the plunger assembly 110 when the injection is resumed. According to other embodiments, the indicator 290 may be irreversibly decoupled from the plunger assembly 110 so that the condition of the injector 100 when an error in administration occurred would be preserved. Preserving the condition of the injector 100 may be useful in assisting the patient or caregiver in their determination for future action based on the amount administered through the intended method of administration (i.e., prior to the occurrence) and the patient's overall disease/therapy conditions.

For example, the plunger assembly 110 may include a plunger arm 140 attached to the plunger 112, as illustrated in FIG. 14. According to such an embodiment, the indicator 290 may be mechanically coupled to the plunger arm 140 through a gear train 292 having at least one gear 294 that is moveable into and out of engagement. The proximity sensor 120 may be coupled to the at least one gear 294 to move the at least one gear 294 out of engagement and decouple the indicator 290 from the plunger arm 140 with the proximity sensor 120 in the first sensor state.

According to the embodiment illustrated in FIGS. 14 and 15, the gear train 292 includes the moveable pinion gear 294, as well as two racks 296, 298 formed on facing surfaces 300, 302 of the plunger arm 140 and the indicator 290. When the gear 294 engages the racks 296, 298 simultaneously, as shown in FIG. 15, the gear 294 transmits motion of the plunger arm 140 to the indicator 290. When the gear 294 is disengaged from rack 296, as shown in FIG. 14, the indicator 290 is decoupled from any motion of the plunger arm 140.

The pinion gear 294 is biased toward engagement with the racks 296, 298 by a spring 304. A linkage 306 passes through the gear 294 at a first end 308, and is attached to a further linkage 310 at a second end 312. The linkage 310 may be a flexible linkage (as illustrated), in the form of a string or cord. In other embodiments, the linkage 310 may include a rigid mechanical linkage including additional levers, gears, couplings, etc. The depicted flexible linkage 310 may pass about a drum, wheel or pulley 314 and be connected to the proximity sensor 120. The proximity sensor 120 may be defined by a lever 316 having a first end 318 attached to the housing 112 at a pivot 320 and a second 322 that is attached to the linkage 310. The lever 316 may be biased to move clockwise about the pivot 320, as illustrated in FIGS. 14 and 15, by a further spring 324.

Figure 16:
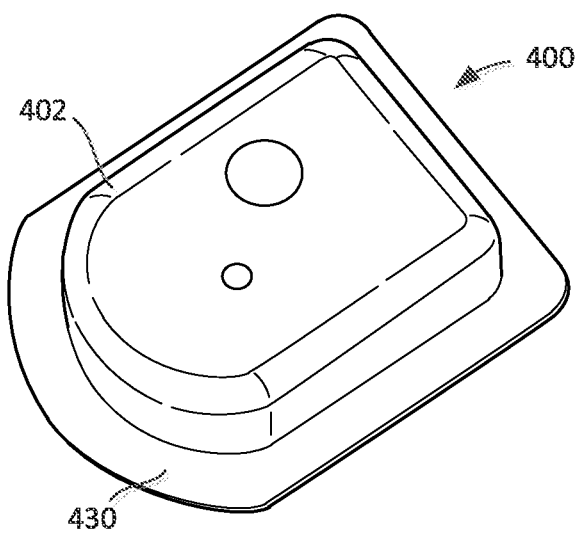
FIG. 16 is a perspective view of an on-body injector, which may incorporate any one of the foregoing embodiments illustrated in FIGS. 1-15.
Figure 17:
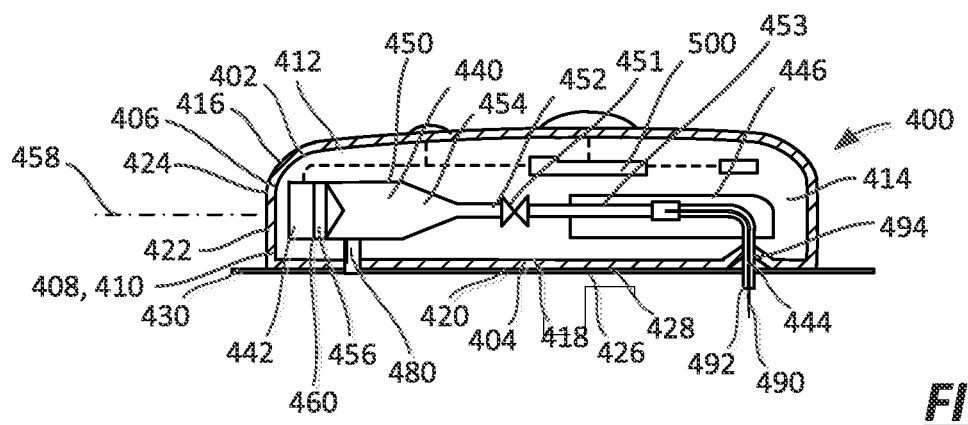
FIG. 17 is a cross-sectional view of the on-body injector of FIG. 16.
Figure 18:
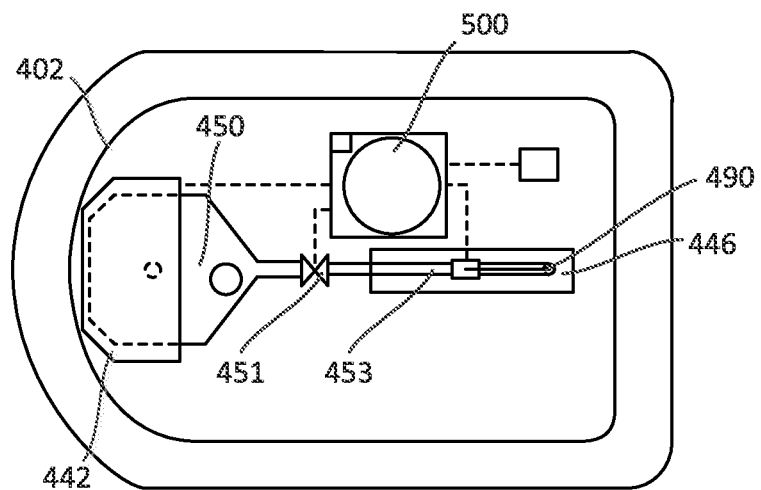
FIG. 18 is a cross-sectional view of the on-body injector of FIG. 16.

The injector 100 of any of the foregoing embodiments may be an on-body injector, the injector 100 comprising a surface having adhesive applied thereto to attach the injector 100 to a body of a patient. For example, FIGS. 16-18 illustrates an on-body injector 400 that may incorporate any of the embodiments illustrated in FIGS. 1-15. In some embodiments, the injector 400 may be a wearable, disposable system. The injector 400 may include a disposable housing 402 that may be attached to a patient or wearer with adhesive, for example.

The disposable housing 402 may be made of a plastic material. As seen in FIG. 17, the housing 402 may be defined by two sections, a plate 404 that is applied against the wearer's skin, and a dome 406 that is attached to the plate 404, preferably by a seal at an interface between a peripheral edge 408 of the plate 404 and a peripheral edge 410 of the dome 406.

As shown in FIG. 17, the housing 402 has an interior surface 412 defining an interior space 414, and an exterior surface 416. In particular, the plate 404 has an interior surface 418 and an exterior surface 420, and the dome 406 has an interior surface 422 and an exterior surface 424. According to the illustrated embodiment, the interior surface 412 of the housing 402 is defined by the interior surfaces 418, 422 of the plate 404 and the dome 406, while the exterior surface 416 of the housing 402 is defined by the exterior surfaces 420, 424 of the plate 404 and dome 406.

The housing 402 may be attached to the skin of the wearer. In some embodiments, an adhesive may be used. The adhesive may be adapted to releasably secure the housing to skin during a single application. As shown in FIG. 16, the adhesive is disposed in a layer 426 on a portion 428 of the exterior surface 416 of the housing 402, and in particular on the exterior surface 420 of the plate 404. The adhesive is covered with a removable, disposable sheet 430 prior to application of the housing 402 to the skin of the wearer.

As seen in FIGS. 17 and 18, a reservoir 440, a drive 442, a cannula (or structure, see below) 444, and an inserter 446 are disposed in the housing 402. According to the illustrated embodiment, the reservoir 440 may be defined at least in part by a combination of a rigid-walled cylinder or bore 450 having a port 452 at a first end 454 and a plunger 456 fitted to move along a longitudinal axis 458 of the cylinder 450 between a second end 460 and the first end 454 to force medical fluid or drug product out of the reservoir 440 through the port 452 (FIG. 17). The movement of the plunger 456 may be caused by the operation of the drive 442. Additionally, as shown, a valve 451 can be disposed at the exit of the port 452 between the reservoir 440 and a delivery line 453 that is fluidly coupled to the cannula 444.

The drive 442 may include a plunger arm and a spring. The plunger arm may be in contact at least at a first end of the plunger 456 to urge the plunger 456 along the cylinder 450, and the spring may be coupled to the plunger arm to cause the plunger arm/plunger 456 to move along the longitudinal axis 458. The combination of the plunger arm and spring may also be referred to as one example of a drive or an actuator. Other mechanisms, such as pressurized gases, materials undergoing phase changes and the like, may be used as the drive 442 to apply a force to the plunger 456 to move the plunger 456 along the cylinder 450. To this extent, the drive 442 may be constructed according to the embodiments disclosed above relative to FIGS. 1-12, or any other embodiment capable of serving the intended purpose.

According to other embodiments, a non-rigid collapsible pouch may be substituted for the rigid-walled cylinder 450 and the plunger 456 illustrated in FIG. 17. In embodiments where the reservoir 450 is in the form of a non-rigid collapsible pouch, a spring-based mechanical system may be used to compress and pressurize the reservoir 450. In other embodiments, a non-mechanical system may be used to move the plunger 456 or compress the non-rigid collapsible reservoir. For example, a gas-generating system may be used, including a two-component system wherein the components are kept apart until the gas is to be generated, in which case they are combined. In some embodiments, a swellable gel may be used, wherein the introduction of water from a source internal to the device causes the gel to increase in dimension to move the plunger or compress the reservoir. As a further example, a propellant reservoir may be opened and the propellant discharged to move the plunger 456 or compress the reservoir. Embodiments of the present disclosure could be used to prevent motion of the structures used to move the plunger 456 or compress the reservoir, thereby limiting such motion if the injector 400 were to separate from the patient during delivery.

According to certain embodiments, the reservoir 440 may be a pre-filled container, such as a pre-filled cartridge or a pre-filled syringe. Alternatively, the injector 400 may include a fill port 480 in fluid communication with the reservoir 440, the fill port 480 adapted to receive a luer tip of a syringe, although a rubber septum may be used instead, for example. In use, a healthcare provider may inject the medical fluid or drug product from the syringe through the fill port 480 into the reservoir 440, and the syringe may be provided as a pre-filled syringe (filled with any of the materials mentioned above) to the healthcare provider with the delivery injector 400 as a kit.

The cannula (or structure) 444 may have a retracted state wherein a pointed end 490 (or, the entire cannula 444) may be withdrawn inside the housing 402 and a deployed state wherein the pointed end 490 projects from the housing 402, the inserter 446 moving the cannula (or structure) 444 from the retracted state to the deployed state. In some embodiments, the injector 400 includes a proximity sensor 120 similar to any one of the proximity sensors 1210 described above and which may extend from the housing 402 (specifically, the plate 404) in a similar fashion to the cannula 444, moving between extended and retracted states.

The cannula 444 may be hollow, and may be used to administer the medical fluid or drug product directly to the patient. Alternatively, the structure 444 may be used in conjunction with a cannula 492 fitted about the structure 444, the structure 444 being used to insert the cannula 492 into the patient through the injection site, and the medical fluid or drug product passing through the catheter 492 into the patient during administration. The injector 400 may, according to certain exemplary embodiments, use a needle to automatically insert a soft cannula into the subcutaneous tissue with the needle being withdrawn prior to passage of medical fluid or drug product through the soft cannula.

As illustrated in FIG. 17, the housing 402 (specifically the plate 404) may have an aperture or opening 494 to permit the cannula (or structure) 444 (and optionally cannula 492) to pass therethrough. According to certain embodiments, the aperture 494 may be unobstructed, such that there is no impediment or obstacle to the movement of the cannula 444 (and catheter 492) through the opening 494. However, to better maintain the sterility of the cannula 444 and the device's container closure integrity (CCI), a septum may be disposed in or over the aperture 494.

The septum, which may be made of a rubber, may be disposed between the cannula 444 (and the space 414) and the patient's skin with the needle 444 in the retracted state. In the deployed state, at least a portion of the needle 444 (i.e., the pointed end 490) will extend from the space 414 through the septum. As such, the septum is always present as a barrier between the interior space 414 and the external environment.

In some embodiments, the injector 400 includes a controller 500. The controller may include at least one processor and memory, the processor programmed to carry out the actions that the controller is adapted to perform, and the memory, including one or more tangible non-transitory readable memories, having executable instructions stored thereon, which instructions when executed by the at least one processor may cause the at least one processor to carry out the actions that the controller is adapted to perform. In other embodiments, the controller may include circuitry that carries out the actions that the controller is adapted to perform. By way of example and not limitation, the controller 500 may be adapted to carry out any one of the methods described above relative to the drug delivery system.

According to certain embodiments of the present disclosure, the lock and proximity sensor may be defined by a single structure, such as a plate or lever, or an assembly of structures, which collectively provide the function. Alternatively, the lock may be a structure defined separately from the proximity sensor. In such a case, the movement of the proximity sensor may be detected through the use of a switch, such as a mechanical switch or optical switch, which switch may be coupled to the controller 500 and may provide information in the form of a signal (or signals, or an absence of signal (low vs. high)) to the controller 500 when the proximity sensor moves or changes positions or states. In some embodiments, the lock can be the valve 451 connected to the controller 500, as depicted in FIGS. 17 and 18, and the proximity sensor can include an electrical sensor (e.g., a Hall effect sensor) or an electromechanical sensor (e.g., a linear variable differential transformer (LVDT)), for example, mounted within the housing for detecting the position of the movable cannula 444 or other movable proximity sensor mounted to the housing. The controller 500 may thus be operatively coupled to the valve 451, and may be capable of transmitting information to the valve 451 in the form of a signal for changing the state of the valve 451 between positions or states in response to the signal received from the switch or other device coupled to the cannula 444 or other proximity sensor. For example, the controller 500 may be coupled to an actuator, such as a linear actuator, that is capable of moving the valve 451 between opened and closed positions or states.

In some embodiments, other advantages of using the controller 500 can include defining the state of the lock or valve 451 as reversible or irreversible. For example, in some embodiments, the proximity sensor may have not only first and second states, but also one or more third states (e.g., intermediate states), where the lock (e.g., valve 451) may transition from occupying a reversible condition to an irreversible condition. This functionality could be therefore achieved through the use of the controller 500 in operable communication with the proximity sensor and lock (e.g., valve 451). In this manner, the sensitivity or threshold for converting the lock condition from reversible to irreversible could be specifically managed by way of the logic or software stored on a memory of the controller 500 based on the specific patient, the specific medical fluid or drug product being administered, or generally any other parameter.

Figure 21:
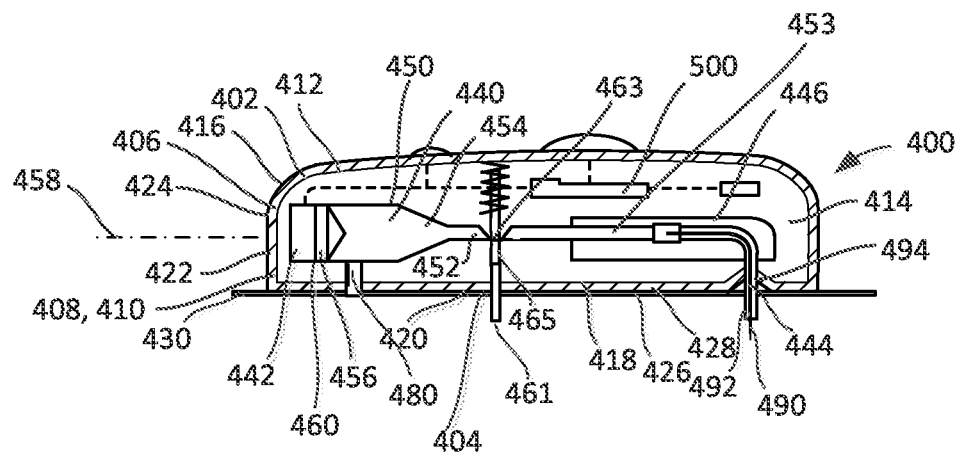
FIG. 21 is a cross-sectional view of an embodiment of a drug delivery device with a proximity sensor and lock including a movable plate in a first, off-body state.
Figure 22:
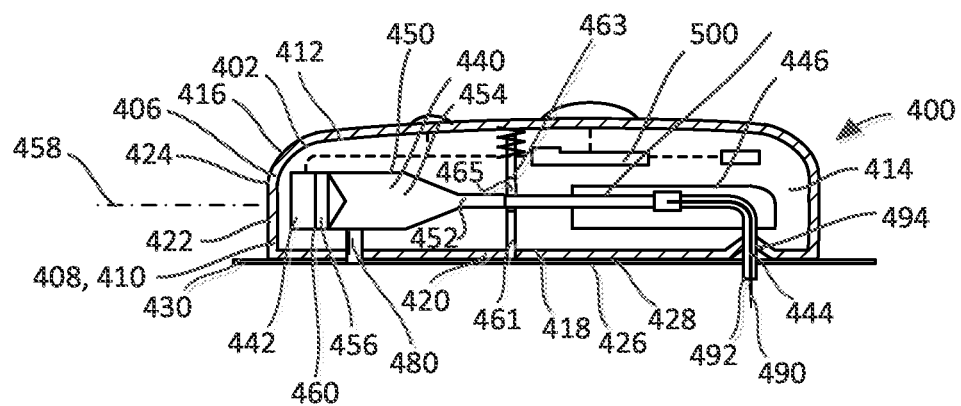
FIG. 22 is a cross-sectional view of the embodiment of FIG. 21 with the proximity sensor and lock in a second, on-body state.

While the lock in FIGS. 17 and 18 has been described as a valve 451, in other embodiments, the lock can take other forms. For example, FIGS. 21 and 22 depict an alternative version of the injector 400, wherein the lock includes a movable plate 461 similar to the proximity sensor 120 described with respect to FIGS. 1-3, for example. The plate 461 is spring biased into the position illustrated in FIG. 21 such that similar to prior embodiments, upon application of the injector 400 to a patient's skin, the plate 461 retracts into the housing 402 and into the position depicted in FIG. 22. As shown, the plate 461 also includes an aperture 465 through which the fluid line 453 of the injector 400 passes. In FIGS. 21 and 22, the fluid line 453 is a flexible line. And, in FIG. 21, an interior edge 463 of the aperture 465 in the plate 461 bears down against an upper sidewall of the fluid line 453 such that the plate 461 pinches the fluid line closed. In this manner, the interior edge 463 of the aperture 465 in the plate 461 limits or prevents fluid in the reservoir 440 from travelling past the pinched portion of the fluid line 453. The plate 461 thus serves as the lock. When the injector 400 is applied to a patient's skin, the plate 461 retracts sufficiently far into the housing that the interior edge 463 of the aperture 465 moves out of engagement with the fluid line, as shown in FIG. 22, such that medical fluid or drug product stored in the reservoir 440 can freely pass through the fluid line 453 under the operation of the drive 442.

The injector of any of the foregoing embodiments may be a hand-held autoinjector 600, the injector comprising a needle shield that defines the proximity sensor. See FIGS. 19 and 20. The autoinjector 600 may include a housing 610 in which may be disposed assemblies or structures that insert or enable insertion of a cannula into the patient, and that inject a medical fluid or drug product from the reservoir through the cannula into the patient. According to certain embodiments, the same assemblies or structures that insert the cannula into the patient may also allow flow of the medical fluid or drug product from the reservoir through the cannula into the patient. The autoinjector 600 may also include assemblies or structures that connect the cannula to the reservoir, that withdraw the cannula into the housing 610, or that deploy other structures that will prevent contact with the cannula once the cannula has been removed from the patient. The specific embodiment of the autoinjector 600 discussed below is provided by way of example and not of limitation. In some embodiments, the autoinjector 600 may or may not include assemblies or structures that direct or force insertion of the cannula (e.g., needle) into the patient. In some embodiments, the cannula may be substantially fixed relative to the housing of the autoinjector 600 such that insertion of the cannula into the patient simply results from moving the cannula into contact with the patient.

In some embodiments, the drug delivery system 600 includes a reservoir 612 and a cannula 614 having a first end 616 that may be connected or connectable in fluid communication to the reservoir 612 and a second end 618 that may be inserted into a patient. The cannula 614 may be, for example, a rigid needle having a beveled edge that may be sized such that the second end 618 of the needle 614 is received under the skin so as to deliver a subcutaneous injection of the medical fluid or drug product within the reservoir 612. The first end 616 of the needle 614 may be disposed through a wall 620 of the reservoir 612, and thus be connected in fluid communication with the reservoir 612. As illustrated, the first end 616 of the needle 614 may be disposed only partially through the wall 620 (which wall 620 may be a resealable septum or stopper, for example) such that the first end 616 of the needle 614 may not be connected in fluid communication with the reservoir 612 until the second end 618 of the needle 614 is inserted into the patient. So configured, the wall 620 of this embodiment is a lock, as used herein, and as will be described. Moreover, in some embodiments, once removed from the patient, the first end 616 of the needle 614 may again become disconnected from fluid communication with the reservoir 612. In such a circumstance, the first end 616 of the needle 614 may be described as connectable in fluid communication with the reservoir 612, although it will be recognized that there are other mechanisms by which the first end 616 of the needle 614 may be connectable, but not connected, in fluid communication with the reservoir 612.

In some embodiments, the drug delivery device 600 includes a shield 622 that may be deployed at least after the injection has been completed to limit access to the second end 618 of the needle 614. According to certain embodiments, the shield 622 may have a biasing element (such as a spring) that extends the shield 622 from the housing 610 such that a distal end 626 of the shield 622 extends beyond the second end 618 of the needle 614 except when the shield 622 is disposed against the skin and the injection of the needle 614 is actuated. In fact, the injection of the needle 614 may be actuated according to certain embodiments of the autoinjector 600 by disposing the distal end 626 of the shield 622 on or against the skin of the patient. According to certain embodiments of the present disclosure, the shield 622 may define the proximity sensor 120.

In some embodiments, the drug delivery device 600 includes at least one drive 630 that may be used to insert the second end 618 of the needle 614 into the skin of the patient, and to inject the medical fluid or drug product from the reservoir 612 through the needle 614 into the patient. The drive 630 may include one or more springs, according to certain embodiments. In other embodiments, the drive 630 may include a source of pressurized gas or a source of a material that undergoes a phase change, such that the escaping gas or phase changing material that provides a motive force that may be applied to the reservoir 612 to eject the medical fluid or drug product therefrom. According to still other embodiments, the drive 630 may include an electromechanical system, such as a motor.

The drive 630 may cooperate with a wall 632 of the reservoir 622 to move that wall 632 toward the patient's skin. In accordance with such an embodiment, the wall 632 may be a stopper that is received within a bore 634, and which may move along the bore 634 from a first end to a second end to inject the medical fluid or drug product from the reservoir 612. The drive 630 may also cooperate with the wall 632 and/or the bore 634 to move the reservoir 612 relative to the housing 610 so as to move the second end 618 of the needle 614 relative to the housing 610 and into the patient. According to those embodiments wherein the drive 630 cooperates with the stopper 632, this may occur before the first end 616 of the needle 614 is in fluid communication with the reservoir 612. According to those embodiments wherein the drive cooperates with the bore 634, the drive may include one component (e.g., first spring) that cooperates with the bore 634 to move the reservoir 612 and needle 614 relative to the housing 610, and a second component (e.g., second spring) that cooperates with the stopper 632 to move the stopper 632 relative to the bore 634.

In some embodiments, the drive 630 is associated with an actuator 640. The actuator 640 activates the drive to cause the drive 630 to insert the needle 614 and inject the medical fluid or drug product from the reservoir 612 through the needle 614 into the patient. The actuator 640 may, according to certain embodiments, be the shield 622. According to other embodiments, the actuator 640 may be a button that may be depressed by the user once the autoinjector 600 is disposed on or against the patient's skin. While the embodiment illustrated in FIGS. 19 and 20 has the actuator 640 disposed at one end of the device, the actuator 640 could be disposed on the side of the device.

According to certain embodiments, the autoinjector 600 may include at least one processor and memory. The controller may also include or be coupled to a power supply, e.g. a battery. The processor may be programmed to carry out the actions that the controller is adapted to perform and the memory may include one or more tangible non-transitory readable memories having executable instructions stored thereon, which instructions when executed by the at least one processor may cause the at least one processor to carry out the actions that the controller is adapted to perform. Alternatively, the controller may include other circuitry that carries out the actions that the controller is adapted to perform.

Figure 19:
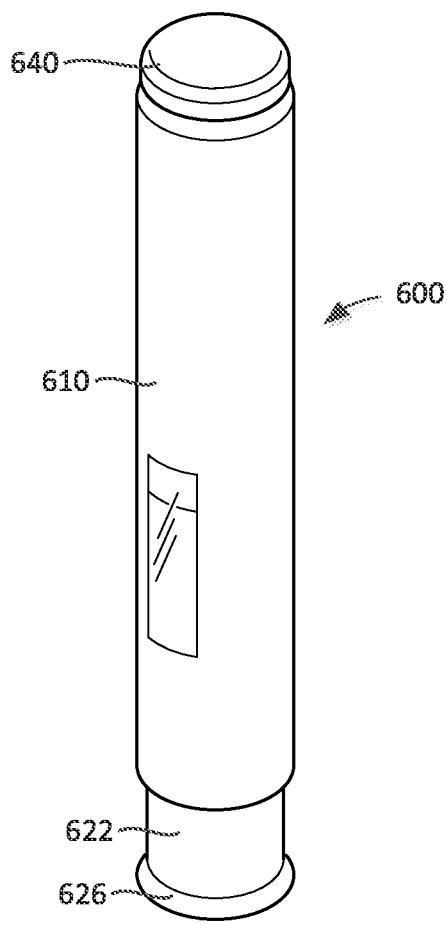
FIG. 19 is a perspective view of an autoinjector, which may incorporate any one of the embodiments illustrated in FIGS. 1-15.

Before the first end 616 penetrates the wall 620, the wall 620 seals the reservoir 612 from communicating with the needle 614 and thereby limits the movement of the wall 632 or stopper in the bore 634. In this way, the wall 620 is a lock, as used herein. But as mentioned above, as the second end 618 of the needle 614 of the autoinjector 600 of FIGS. 19 and 20 is inserted into a patient, the first end 616 of the needle 614 penetrates the wall 620 to become in fluid communication with the reservoir 612. In some embodiments, once the second end 618 of the needle 614 is removed from the patient, the first end 616 of the needle 614 may again become disconnected from fluid communication with the reservoir 612 by, for example, being drawn back through the wall 620 at least such that the first end 616 of the needle 614 no longer resides within the reservoir 612, but rather resides inside of the wall 620 or, said another away, resides at a point between opposing surfaces of the wall 620. In this way, the wall 620 can automatically seal the opening through which the first end 616 of the needle 614 previously passed into the reservoir, and thereby locks the fluid delivery mechanism.

Figure 20:
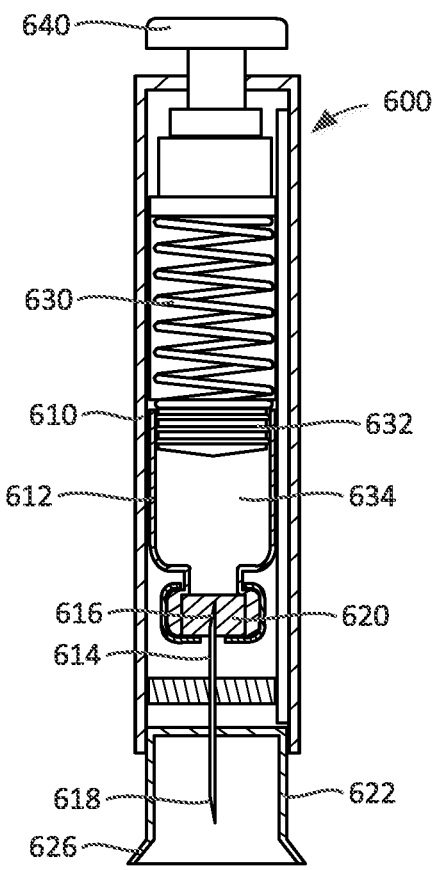
FIG. 20 is a cross-sectional view of the autoinjector of FIG. 19.
Figure 23:
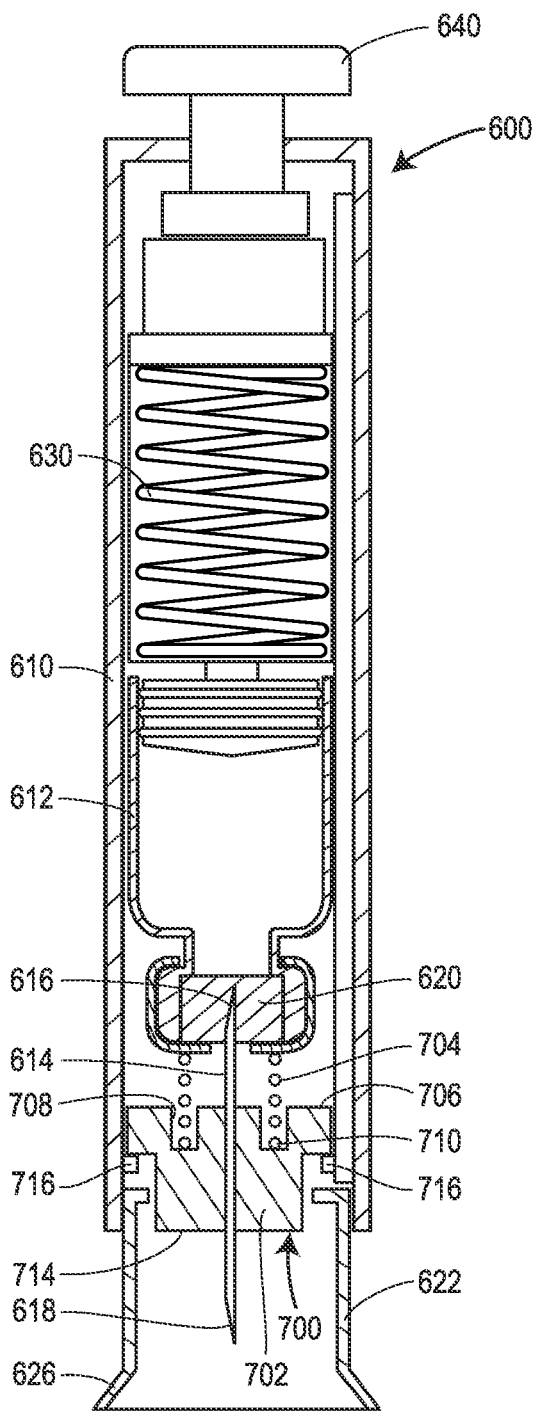
FIG. 23 is a cross-section view of an alternative version of the auto-injector of FIGS. 19 and 20 including a needle assembly that serves as a proximity sensor.
Figure 24:
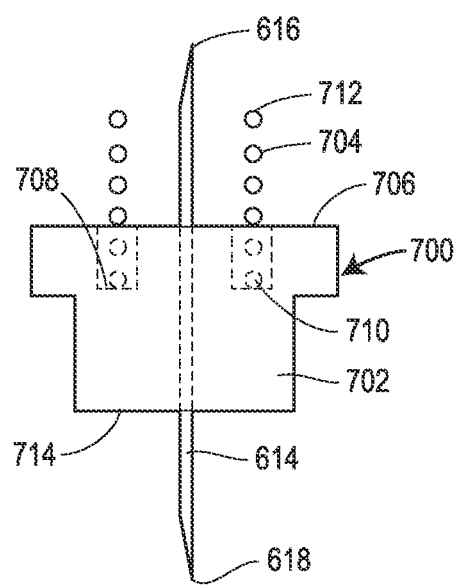
FIG. 24 is a side view of the needle assembly of FIG. 23.

FIGS. 23 and 24 illustrate an alternative version of the autoinjector 600 depicted in FIGS. 19 and 20 for facilitating this functionality. In FIGS. 23 and 24, the autoinjector 600 includes a needle assembly 700 for disconnecting the needle 614 from fluid communication with the reservoir 612 when the needle 614 is removed from the patient. As illustrated, the needle assembly 700 includes a retainer 702 and a biasing member such as spring 704. The retainer 702 is fixed to the needle 614 and slidably disposed in the housing 610 adjacent to the shield 622. The spring 704 can be a coil spring and is disposed between the wall 620 of the reservoir 612 and the retainer 702. In the depicted version, a top surface 706 of the retainer 702 defines an annular recess 708 into which a first end 710 of the spring 704 is seated. A second end 712 of the spring 704 is seated against the wall 620 (or a component surrounding the wall 620). So configured, the spring 704 biases the needle assembly 700 away from the reservoir 612 and the wall 620 (i.e., downward relative to the orientation of the autoinjector 600 depicted in FIG. 23).

Accordingly, when the second end 618 of the needle 614 is inserted into a patient, a bottom surface 714 of the retainer 702 bears against the patient's skin and therefore serves as the proximity sensor in this embodiment. As a force is applied to the autoinjector 600 in the direction of the patient's skin, the needle assembly 700 moves into the housing 610 against the force of the spring 704 such that the first end 616 of the needle 614 fully penetrates the wall 620 and becomes in fluid communication with the reservoir 612. This allows medicament in the reservoir 612 to pass into the first end 616 of the needle 614 for patient administration. When the needle 614 is removed from the patient, the spring 702 naturally biases the retainer 702 back into the position depicted in FIG. 23 which in turn draws the needle 614 with it because the needle 614 and retainer 702 are fixed together. In the version shown in FIG. 23, the housing 610 of the autoinjector 600 further includes one or more stops 716 carried by the inside of the housing 610 adjacent to the shield 622. As the spring 702 biases the retainer 702 away from the reservoir 612, the retainer 702 comes into contact with the stop(s) 716. The stop(s) 716 therefore limit the displacement of the retainer 702 and needle 614 away from the reservoir 612 such that when the retainer 702 engages the stop(s) 716, the first end 616 of the needle 614 is fully withdrawn from and out of fluid communication with the reservoir 612. In the depicted version, this also means that the first end 616 of the needle 614 resides within the wall 620, which serves as the lock. That is, the wall 620 in this configuration limits further movement of the wall 623 or stopper by sealing the flow path through the needle 614 when the device is removed from the patient. In this version, the wall 620, as the lock, is reversible because when the second end 618 of the needle 614 is subsequently re-inserted into a patient, for example, the needle assembly 700 can again move into the housing 610 against the force of the spring 704 such that the first end 616 of the needle 614 fully penetrates the wall 620 and becomes in fluid communication with the reservoir 612. In other versions, the device may include additional structures that prevent such reversible action from occurring.

The present disclosure describes various systems and methods for use with a drug delivery device. The system, methods or drug delivery device can comprise use of a medical fluid or drug product listed below, with the caveat that the following list should neither be considered to be all inclusive nor limiting. The medical fluid or drug product will be contained in a reservoir. In some instances, the reservoir is a primary container that is either filled or pre-filled for treatment with the medical fluid or drug product. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858) as well as erythropoietin molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047;

6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4;

Myostatin binding proteins, peptibodies, and related proteins, and the like, including myostatin specific peptibodies, particularly those described in US Publ. No. 2004/0181033 and PCT Publ. No. WO 2004/058988, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/37242 and in US Publ. No. 2005/112694, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1;

Interleukin 1-receptor 1 ("IL1-R1") specific antibodies, peptibodies, and related proteins, and the like, including but not limited to those described in U.S. Publ. No. 2004/097712A1, in parts pertinent to IL1-R1 specific binding proteins, monoclonal antibodies in particular, especially, without limitation, those designated therein: 15CA, 26F5, 27F2, 24E12, and 10H7, as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8 (N); TN8-14 (N); Con 1 (N), also including anti-Ang 2 antibodies and formulations such as those described in PCT Publ. No. WO 2003/030833, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, as disclosed in the foregoing publication;

NGF specific antibodies, peptibodies, and related proteins, and the like including, in particular, but not limited to those described in US Publ. No. 2005/0074821 and U.S. Pat. No. 6,919,426, particularly as to NGF-specific antibodies and related proteins in this regard, including in particular, but not limited to, the NGF-specific antibodies therein designated 4D4, 4G6, 6H9, 7H2, 14D10 and 14D11, as disclosed in the foregoing publication;

CD22 specific antibodies, peptibodies, and related proteins, and the like, such as those described in U.S. Pat. No. 5,789,554, as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof;

Also among non-limiting examples of anti-IGF-1R antibodies for use in the methods and compositions of the present disclosure are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.32, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (74), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein);

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing US Publication and in Thakur et al., Mol. Immunol. 36:1107-1115 (1999). Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, as to TALL-1 binding proteins, particularly the molecules of Tables 4 and 5B, as disclosed in the foregoing US Publications;

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in US Publ. No. 2009/0234106, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, particularly in parts pertinent to proteins that bind TGF-beta;

Amyloid-beta protein specific antibodies, peptibodies, related proteins, and the like, including but not limited to those described in PCT Publ. No. WO 2006/081171, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, particularly in parts pertinent to proteins that bind c-Kit and/or other stem cell factor receptors;

OX40L specific antibodies, peptibodies, related proteins, and the like, including but not limited to those described in U.S. application Ser. No. 11/086,289, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-051 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti- CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX00 (Lei et al., 2013, World Journal of Gastroenterology, 19:5138-5143); G207, 1716; NV1020; NV12023; NV1034 and NV1042 (Vargehes et al. 2002, Cancer Gene Ther, 2002, 9 (12): 967-978).

Also included are TIMPs. TIMPs are endogenous tissue inhibitors of metalloproteinases (TIMPs) and are important in many natural process. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. 61/782,613, U.S. 61/798,160, U.S. 61/802,988, and US 61/940,67.

Also included are antagonistic antibodies for human calcitonin gene-related peptide (CGRP) receptor and bispecific antibody molecule that target the CGRP receptor and other headache targets. Further information concerning these molecule can be found in WO2A075238A1.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT/2013/075773.

Although the preceding text sets forth a detailed description of different embodiments of the disclosure, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, that would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed:

1. An on-body injector comprising:
    a reservoir filled or configured to be filled with a drug;
    a cannula;
    a drive operable to move the drug out of the reservoir;
    a proximity sensor having a first sensor state when the proximity sensor is not in contact with skin of a patient and a second sensor state when the proximity sensor is in contact with the skin of the patient, wherein the proximity sensor is configured to output at least one electrical signal as a result of changing from the first sensor state to the second sensor state;
    a lock having a first position to prevent the drive from moving the drug out of the reservoir when the proximity sensor is in the first sensor state and the lock having a second position permitting the drive to move the drug out of the reservoir when the proximity sensor is in the second sensor state, wherein the lock is operably coupled to the proximity sensor such that the proximity sensor changing from the first sensor state to the second sensor state causes the lock to move from the first position to the second position; and
    an actuator configured to move the lock between the first position and the second position.

2. The on-body injector of claim 1, comprising a housing, wherein the reservoir, cannula, and drive each is disposed at least partially within the housing.

3. The on-body injector of claim 2, comprising a controller disposed at least partially within the housing and being in communication with the proximity sensor and the lock.

4. The on-body injector of claim 3, the controller being configured to change the lock from the first position to the second position in response to the at least one electrical signal received from the proximity sensor in the second sensor state.

5. The on-body injector of claim 3, wherein the proximity sensor comprises an electrical sensor or an electromechanical sensor.

6. The on-body injector of claim 3, wherein the controller comprises a processor and a memory.

7. The on-body injector of claim 2, wherein the cannula is moveable through an opening in the housing for insertion into the skin of the patient.

8. The on-body injector of claim 7, comprising an inserter disposed at least partially within the housing and configured to move the cannula through the opening for insertion into the skin of the patient.

9. The on-body injector of claim 2, comprising an indicator disposed at an exterior of the housing and configured to visually indicate progress of an injection.

10. The on-body injector of claim 1, wherein the cannula has a pre- operational state wherein the cannula is not connected in fluid communication with the reservoir.

11. The on-body injector of claim 1, comprising a plunger movably disposed in the reservoir, wherein the lock mechanically resists movement of the plunger between first and second ends of the reservoir when the proximity sensor is in the first sensor state.

12. The on-body injector of claim 1, wherein the drive comprises a motor.

13. The on-body injector of claim 1, wherein the drive comprises a source of pressurized gas.

14. The on-body injector of claim 1, comprising a controller configured to receive the at least one electrical signal output by the proximity sensor and control the lock.

15. An on-body injector comprising:
a reservoir filled or configured to be filled with a drug;
a cannula;
a drive operable to move the drug out of the reservoir;
a proximity sensor having a first sensor state when the proximity sensor is not in contact with skin of a patient and a second sensor state when the proximity sensor is in contact with the skin of the patient;
a lock operably coupled to the proximity sensor, the lock having a first position to prevent the drive from moving the drug out of the reservoir when the proximity sensor is in the first sensor state and the lock having a second position permitting the drive to move the drug out of the reservoir when the proximity sensor is in the second sensor state;
an actuator configured to move the lock between the first position and the second position; and
a controller in communication with the proximity sensor, the lock, and the actuator, the controller being configured to change the lock from the first position to the second position in response to a signal received from the proximity sensor in the second sensor state.

16. The on-body injector of claim 15, comprising a housing having an opening, wherein the cannula is moveable through the opening in the housing for insertion into the skin of the patient.

17. The on-body injector of claim 16, comprising an inserter disposed at least partially within the housing and configured to move the cannula through the opening for insertion into the skin of the patient.

18. The on-body injector of claim 15, wherein the cannula has a pre-operational state wherein the cannula is not connected in fluid communication with the reservoir.

* * * * *